United States Patent [19]

Citron et al.

[11] 4,417,306

[45] Nov. 22, 1983

[54] APPARATUS FOR MONITORING AND STORING UTILIZING A DATA PROCESSOR

[75] Inventors: Paul Citron, New Brighton; Dennis G. Hepp, Coon Rapids; Thomas L. Jirak, Plymouth, all of Minn.

[73] Assignee: Medtronic, Inc., Minneapolis, Minn.

[21] Appl. No.: 337,991

[22] Filed: Jan. 7, 1982

Related U.S. Application Data

[63] Continuation of Ser. No. 114,595, Jan. 23, 1980, abandoned.

[51] Int. Cl.³ .......................... G06F 15/42; A61B 5/04
[52] U.S. Cl. ................................... 364/415; 128/702; 128/703; 128/710; 364/417
[58] Field of Search ............................. 364/415–417, 364/900; 128/696, 702–704, 706, 710, 711

[56] References Cited

U.S. PATENT DOCUMENTS

| 3,518,983 | 7/1970 | Jorgensen | 128/702 |
|---|---|---|---|
| 3,779,237 | 12/1973 | Goeltz et al. | 128/702 |
| 3,799,148 | 3/1974 | Rowen | 128/704 |
| 3,820,025 | 6/1974 | Lahr et al. | 128/706 |
| 3,874,370 | 4/1975 | Harris et al. | 128/702 |
| 3,902,479 | 9/1975 | Chaumet | 128/703 |
| 3,909,792 | 9/1975 | Harris et al. | 364/900 |
| 3,946,725 | 3/1976 | Bolshov et al. | 128/706 |
| 4,053,951 | 10/1977 | Hudspeth et al. | 364/415 |
| 4,073,011 | 2/1978 | Cherry et al. | 128/704 |
| 4,124,894 | 11/1978 | Vick et al. | 364/417 |
| 4,193,393 | 3/1980 | Schlager | 128/710 |
| 4,211,238 | 7/1980 | Shu et al. | 128/711 |

Primary Examiner—Errol A. Krass
Attorney, Agent, or Firm—Mason, Fenwick & Lawrence

[57] ABSTRACT

Apparatus for monitoring and storing heart activity signals is disclosed as including a data processor illustratively in the form of a digital microprocessor. The monitoring and storing apparatus comprises a memory comprising first and second pluralities of storage locations, a circuit operating in a real time frame for sampling at a regular rate the patient's heart activity and for storing such sample signals in corresponding locations of said first plurality, an the data processor for processing the signals stored in the first plurality and for storing the processed signals in selected locations of said second plurality. The storage of the signals in the second plurality is performed in a second computer time frame and at a rate faster than the real time sampling rate. A sampling clock provides a sampling clock signal to the sampling circuit whereby the samples of the patient's heart activity are taken. A second computer clock provides computer clock signals to at least a portion of the data processor whereby the processing of the heart activity is effected in the relatively fast computer time frame. The data processor comprises a first portion or means that operates in response to the sample clock signal for evaluating the heart activity signals to determine the existence of a valid heartbeat and a second portion operating in the computer time frame for processing the detected heartbeat and in particular for determining the interval therebetween, which is evaluated to determine whether the heartbeat is occurring with a regular rhythm or not.

39 Claims, 29 Drawing Figures

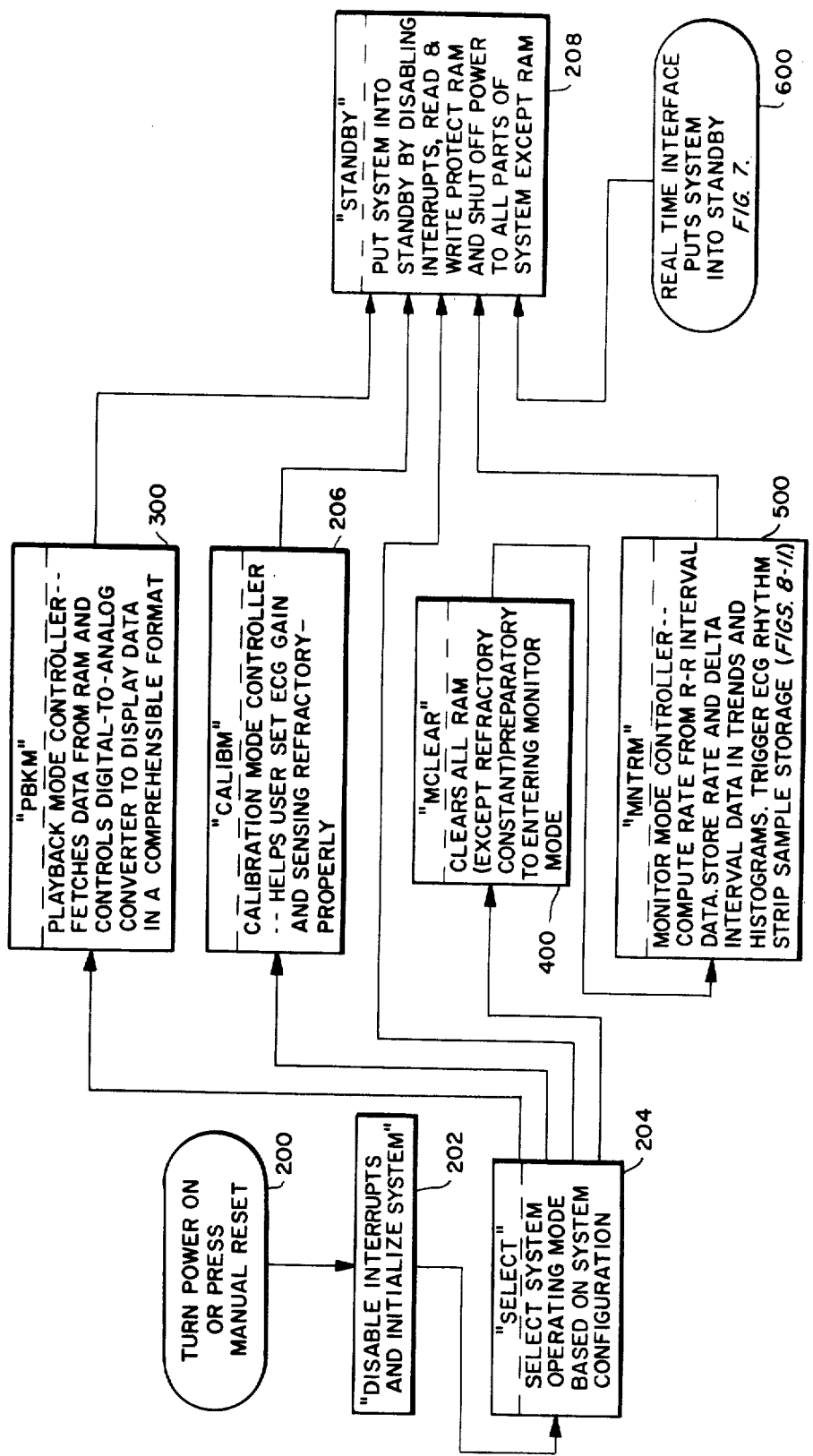

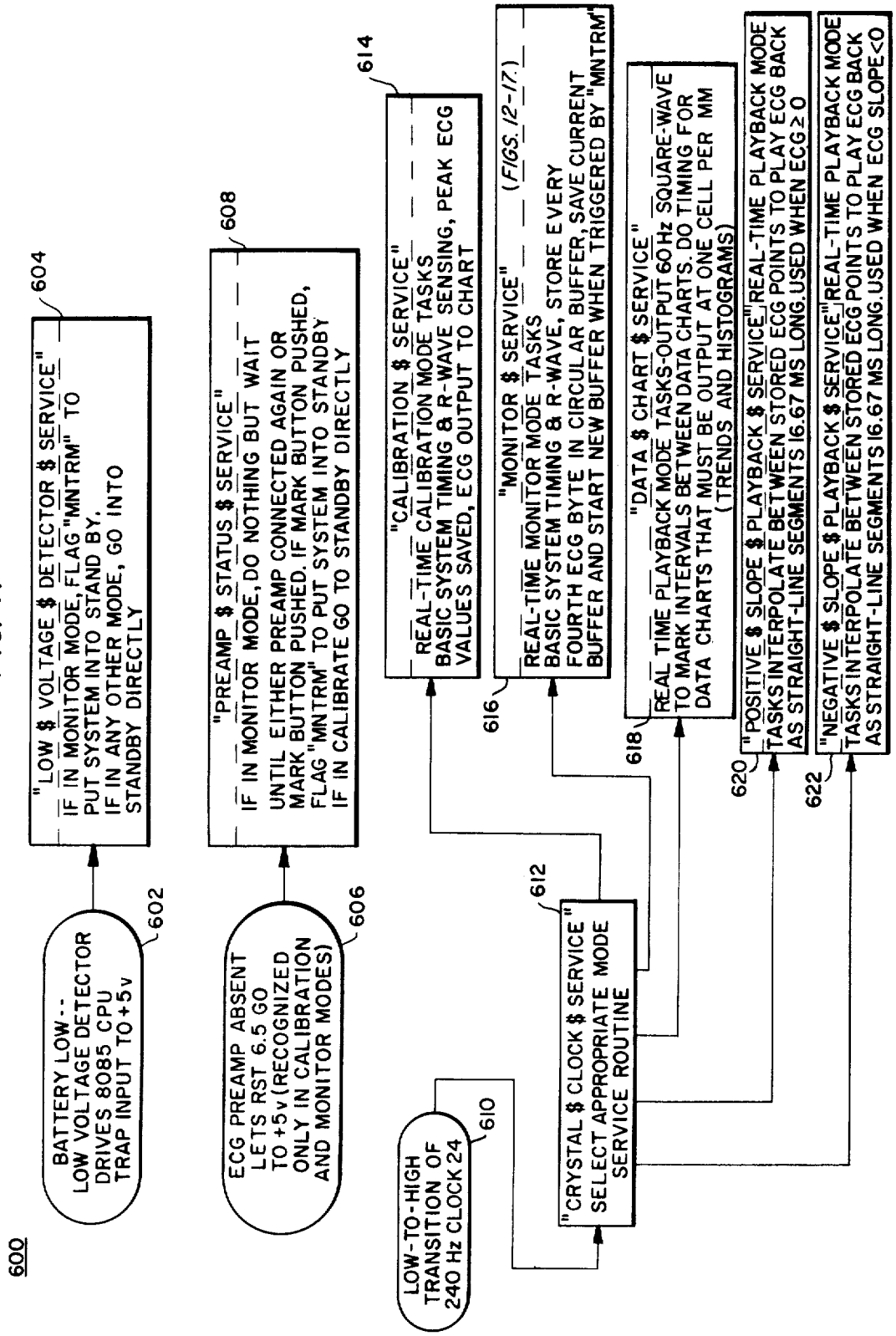

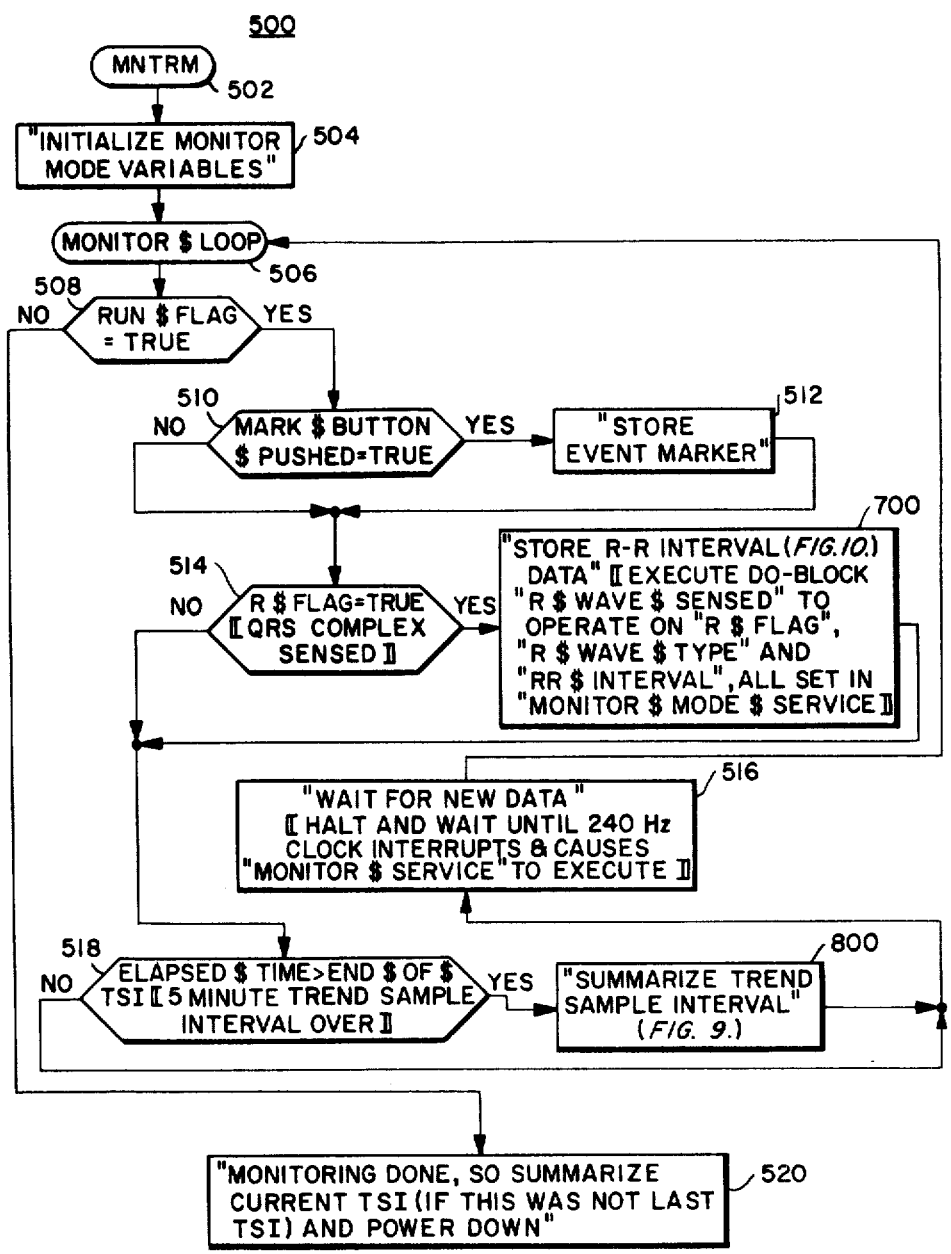

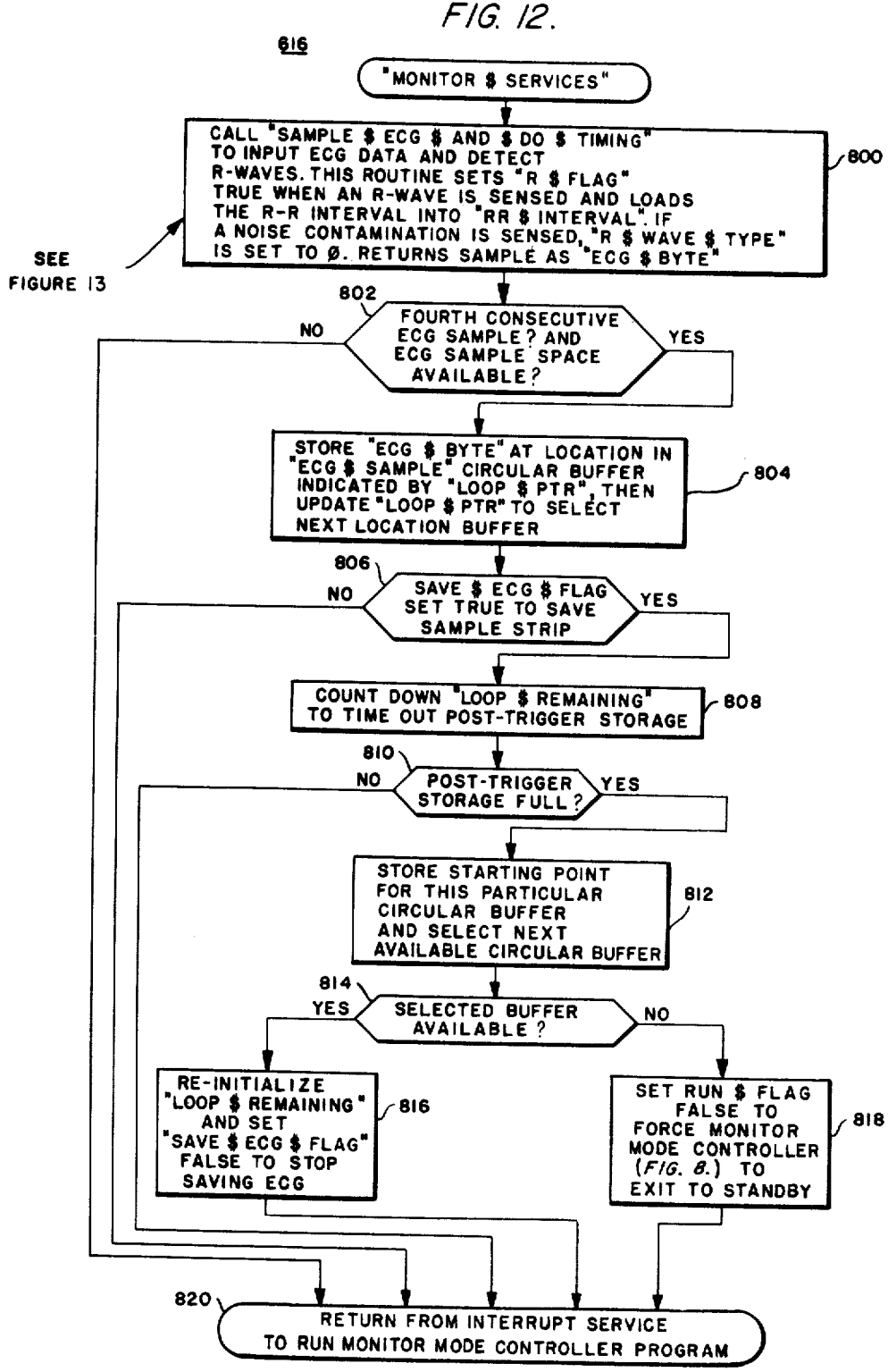

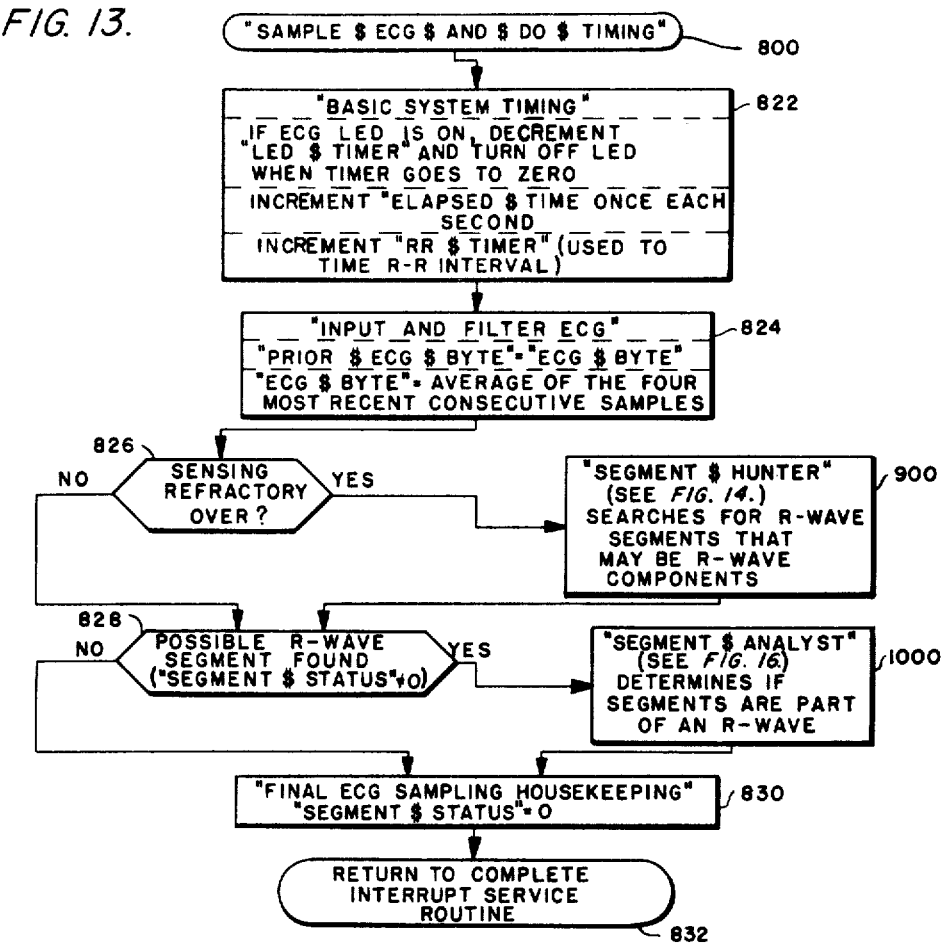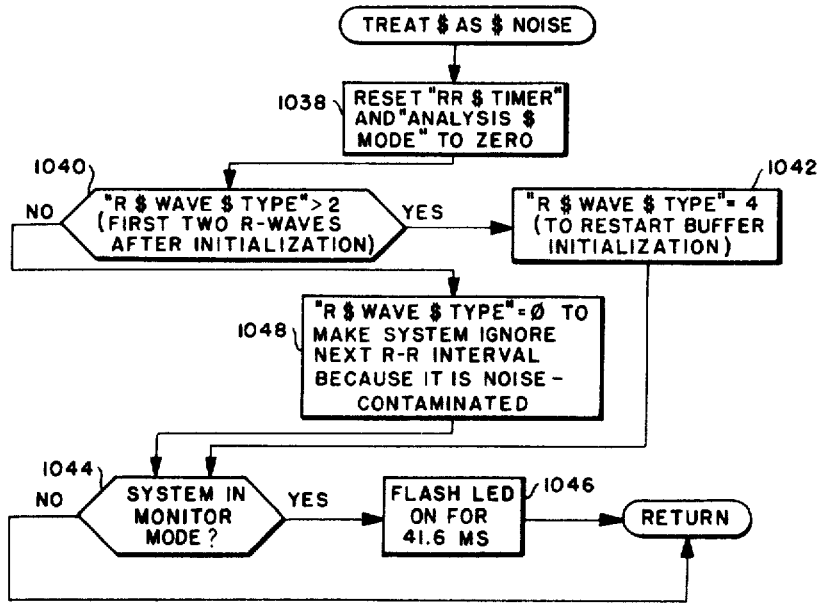

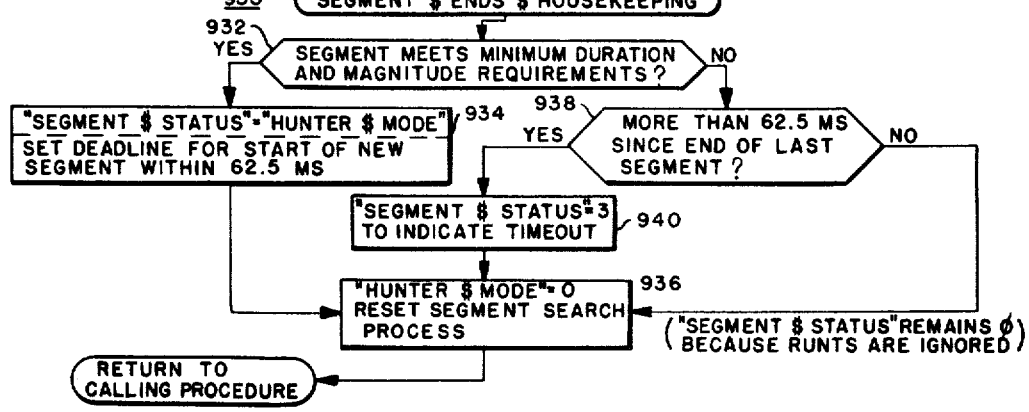

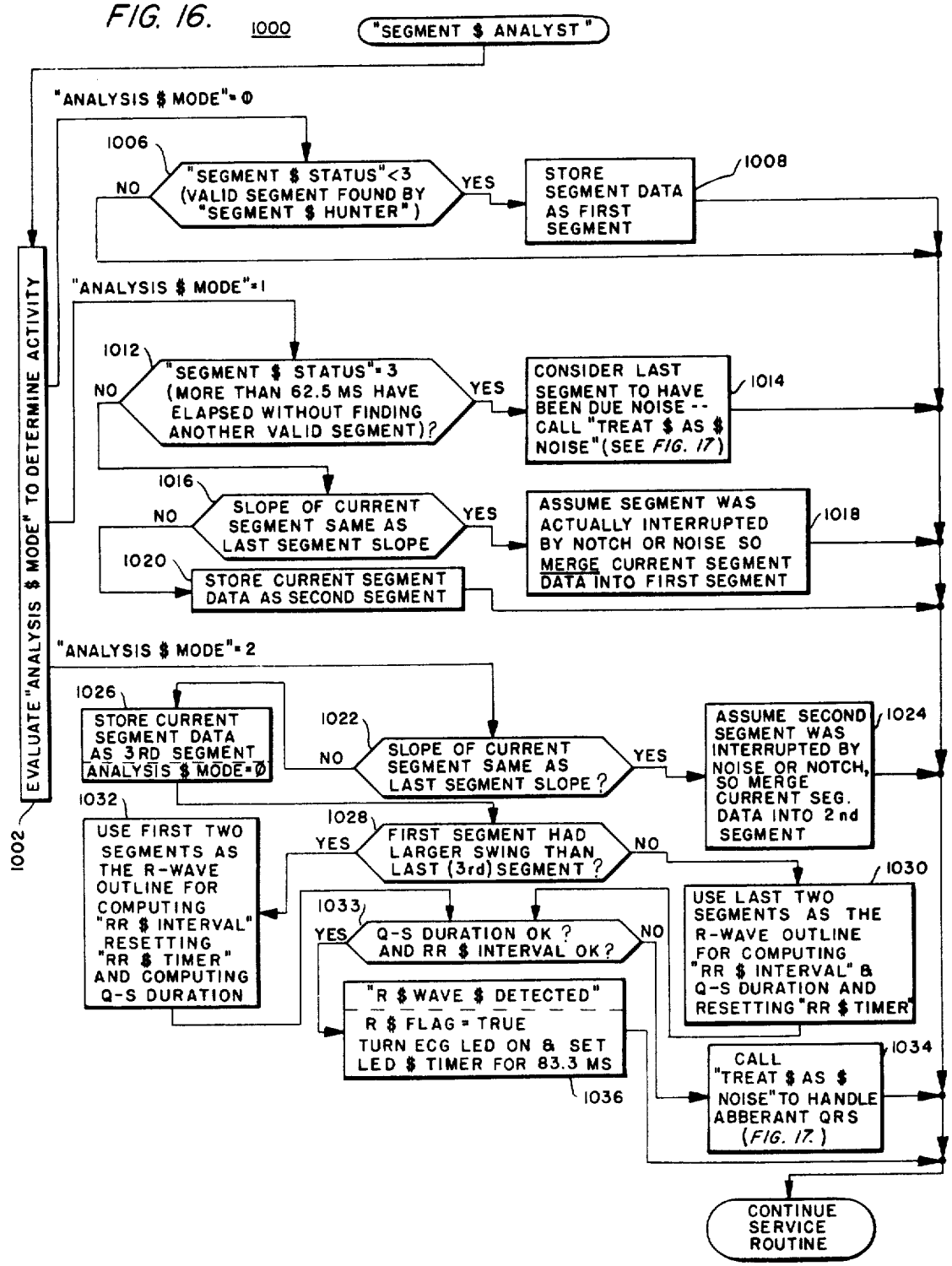

FIG. 18A.
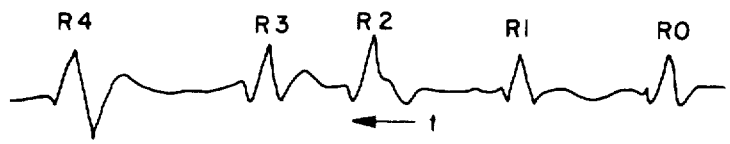
FIG. 18B.
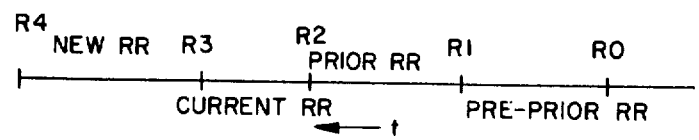
FIG. 18C.
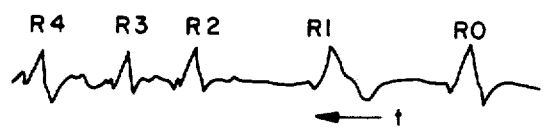
FIG. 18D.
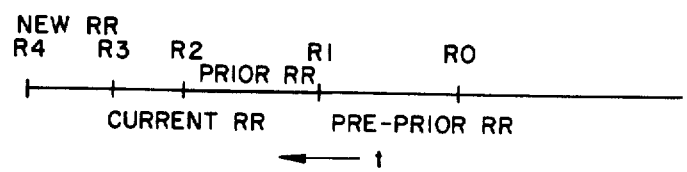
FIG. 19A.  FIG. 19B.
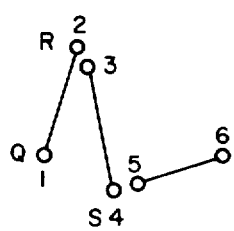 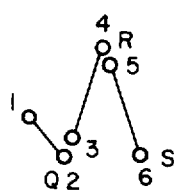
FIG. 19C.

APPARATUS FOR MONITORING AND STORING UTILIZING A DATA PROCESSOR

This is a continuation of application Ser. No. 114,595, filed Jan. 23, 1980, now abandoned.

CROSS REFERENCE TO CO-PENDING APPLICATIONS

Attention is drawn to the following co-pending commonly assigned applications, each incorporated specifically by reference into the specification:
(1) APPARATUS FOR MONITORING AND STORING HEARTBEATS OF A PATIENT, having Ser. No. 114,594 filed on Jan. 23, 1980, now U.S. Pat. No. 4,367,753, by Thomas L. Jirak;
(2) APPARATUS FOR MONITORING THE RHYTHM OF A PATIENT'S HEARTBEAT, having Ser. No. 114,664, and filed on Jan. 23, 1980, now U.S. Pat. No. 4,364,397by Paul Citron, Dennis G. Hepp, and Thomas L. Jirak; and
(3) APPARATUS FOR MONITORING AND STORING A VARIETY OF HEART ACTIVITY SIGNALS, having Ser. No. 114,663, and filed on Jan. 23, 1980, now U.S. Pat. No. 4,360,030 by Paul Citron, Dennis G. Hepp, and Thomas L. Jirak.

DESCRIPTION

TECHNICAL FIELD

This invention relates to apparatus for compacting and storing data indicative of a patient's heart activity.

BACKGROUND OF THE PRIOR ART

The prior art has recognized, as described in the article entitled "The Use of R—R Interval and Difference Histograms in Classifying Disorders of Sinus Rhythm" by P. M. M. Cashman appearing in the January 1977 issue of *Journal of Medical Engineering Technology*, the need to provide heart activity and in particular ECG recording over relatively long period of time from ambulatory patients. The primary objective of such recordings is to permit identification of infrequent and transient disturbances of cardiac rhythm, which may be important in diagnosing patients with vague or inermittent symptoms such as dizzy spells, blackouts, and fainting attacks. While recording for a longer period of time, the physician's interest is to detect short, specific dysrhythmic events which occupy only a small percentage of the total recording time. Such disrhythmic events are considered as singularities in a background rhythm. Typically, the physician is interested not only in the specific disrhythmic event but also the background rhythm which may comprise slower responses of the heart to influences such as drug treatment or psychological stress over long periods of time. In this regard, it may be desirable to compare the long recordings from either different patients or from the same patient at different times.

At present, the use of ambulatory heart monitors, typified by the Holter recorder, is well known in the art. The Holter technique typically records the patient's ECG activity for at least 24 hours. The difficulty with the use of a Holter recorder is that it provided a large volume of information which requires processing and analysis. Such analysis is usually time consuming and expensive. Typically, the review and processing time may be reduced by reading out and displaying the data at increased speeds, typically multiples of 25, 32, 60, and 120 of the normal playback rate. In order to display the heart data, and in particular the QRS complex, with sufficient clarity, it may be necessary to use recording apparati with fequency responses in excess of 12 kHz. This is possible with ultraviolet recorders, fiber optical recording oscilloscopes, or inklet records, all of which are expensive.

The prior art has suggested a variety of apparati for the processing and display of a patient's heart activity data. Such apparatus may include a detector for automatically sensing a dysrhythmia and in response thereto, stores and displays a sample of the patient's ECG either directly onto paper or onto a screen. Further, a contourogram may be provided by a storage oscilloscope or Polaroid camera whereby subsequent lengths of a patient's ECG are displayed one beneath the other. Each such segment or tracelength is proportional to the beat-to-beat interval and the right-hand edge of the trace gives a continuous record of the R—R interval trend. One of the most common methods of presenting ECG data is to provide a heart rate trend wherein the R—R interval is continuously measured and the R—R interval data is segmented into continuous time periods. In particular, the rate or interval of the heartbeat is averaged ot provide a display of average heart rates or intervals for a series of adjacent time periods. For resolving individual beats on a trend plot, it may be preferable to plot the instantaneous rate in a form of a trend plot.

In addition to the methods of display as discussed above, there is the need to identify and to highlight the isolated occurrence of an abnormal or ectopic beat. Typically, the ectopic beat is detected and is counted during the course of the heart monitoring period. Apparatus has been provided to detect premature heartbeat. The degree of prematurity can often be preset by the operator to provide selection of the beats to be detected. The output of such detectors is applied to a counting circuit, a trend recorder, or some form of alarm depending upon the desired application. Several techniques have been used to detect the abnormal shape of the patient's ECG signal including simple integrators, filters, and digital pattern recognition systems. It is contemplated that normal ECG signals are analyzed to determine the limits of occurrence of the peaks of the QRS complexes, and to compare such limits with the incoming signal to determine whether the present ECG signal fits within these predetermined, normal limits.

In more sophisticated systems, the patient's normal ECG signal is detected and stored. In subsequent monitoring, the patient's normal signal is used as a template against which to compare the current heart data. U.S. Pat. No. 4,115,864 discloses such a cardiac monitor, utilizing a computer to control the storage of the patient's normal signal, to process the inputted ECG signal into digital segments, and to compare those segments with corresponding segments of the previously stored normal ECG of the patient. When the stored normal signal does not fit the current signal, an alarm or detector circuit is actuated and the number of occurrences of that ectopic signal is stored within the memory of the computer. The described system is capable of providing a trend history of such ectopic beats in the form of a histogram or trend plot.

In any processing of ECG data, it is necessary to use discrimination techniques to extract a trigger pulse for each cardiac cycle. In most instances, the detection circuit triggers on the R-wave, and it is thus necessary to distinguish the R-wave of the QRS complex from the rest of the signal. It is contemplated that it may be necessary, in the presence of heavy background noise, to terminate the monitoring for the duration of the high level background noise. In other instances, the detection circuitry may provide an alarm so that the operator can intervene.

Noting the desire to provide monitoring for long periods of time of a patient's heart activity, the continuous monitoring by the Holter monitor provides a complete record at relatively inexpensive cost. On the other hand, the methods of processing and compacting the data for simpler, limited display oftentimes requires a more complex system of increased cost. To avoid either pitfall, it has been suggested that the data be presented in the form of an R—R interval histogram as shown in FIG. 1. A histogram presents heart activity data taken over a period of time in a compact manner, wherein the successive intervals between R-waves are computed and are classified as to their duration. As shown in FIG. 1, the X axis is in seconds corresponding to the R—R interval, whereas the Y axis provides the number of beats that occur within each interval. Such a presentation provides a large data reduction in a visual way which allows easy comparison between the histograms of the same patient taken at different times and between different patients. The R—R interval histogram (IH) is formed by generating an array of columns or bins, each corresponding to a range of values of beat-to-beat (or R—R) interval. As each ECG complex is detected, the time interval between it and its predecessor is measured and the total in the appropriate bin incremented. A typical histogram might contain a hundred bins, each having a width of 20 milliseconds, giving a total range of R—R intervals from 0 to 2 seconds. A bin capcity of 4,095 beats (a 12-bit binary word) will permit about 4 hours of normal heart monitoring.

A variation of the R—R interval histogram is the R—R interval difference histogram (IDH), as shown in FIG. 2. The IDH is formed similarly except that the quantity as displayed along the X axis as shown in FIG. 2 is the amount by which the R—R interval changes between successive beats. As shown in FIG. 2, the central bin is designated 0, i.e., 0 difference between successive beats, and a hundred columns provide a range between −1 second through 0 to +1 second, with a bin width of 20 milliseconds. The mean of the interval differences is always very close to 0. The IDH provides an indication of the manner of change of the heartbeat, where the width of the IH is the measure of the spread of heart rates about the mean value. It is apparent that the use of both the IH and the IDH provide the physician with a powerful tool for diagnosis of the patient's heart.

Further, U.S. Pat. No. 4,146,029 describes a system implanted within the body of the patient for dispensing medication into the patient's body. The system is implemented by a microprocessor for the control of the process whereby each QRS complex of the patient's heart is detected as to the length of the QRS complex and to the interval therebetween. A program of comparing the length of the QRS complex to an acceptable length is provided to determine the validity of each QRS complex and further to first calculate the interval between QRS complexes and to compare the measured length to a known or standard length for a particular patient. More specifically, the process compares the length to determine how much shorter the measured ongoing intervals are with regard to the normal length and dependent upon the decrease the length, i.e., the increase of heart rate, the microprocessor controls dispensing apparatus to vary the dosage given to the patient. Included in the appartus is a process for measuring the R—R interval and for accumulating the average of the R—R interval over a given period of time, for example, an hour. The averaged R—R intervals are compared with known standards to variably control the dispensation of medication to the patient.

BRIEF SUMMARY OF THE INVENTION

It is an object of this invention to provide new and improved apparatus for monitoring and storing heart acitvity signals utilizing a data processor illustratively in the form of a digital microprocessor.

It is a further object of this invention to operate the data processor in a most efficient manner to evaluate and store signals indicative of the patient's heart signals.

It is a more specific object of this invention to provide new and improved apparatus for monitoring and storing signals indicative of a patient's heart activity, wherein the apparatus is embodied by a data processing apparatus that operates in a first, relatively slow real time frame to sample the signals of the patient's heart and in a second, relatively fast computer time frame for processing and evaluating the sampled heart signals.

In accordance with these and other objects of the invention, there is provided apparatus fo monitoring and storing electrical signals indicative of a patient's heart activity including means responsive to the patient's heart activity for providing a series of R—R interval signals indicative of the intervals between successive peaks of the patient's heart activity, and evaluating means for examining selected of the series of R—R interval signals to indicate whether the patient's heart signals are regular or disrhythmic.

In a further aspect of this invention, a data processor comprises a first portion or means that operates in response to a sample clock signal for evaluating the heart activity signals to determine the existence of a valid heartbeat. In an illustrative embodiment, the heart activity signals are evaluated to determine segments thereof and thereafter to examine a series of such segments to determine whether a valid heartbeat has been monitored.

In a still further aspect of this invention, the data processor includes a further portion operating in the computer time frame for processing the detected heartbeat and in particular for determining the interval therebetween, and subsequently the heartbeat rate. The manifestations of the intervals between successive heartbeats and the rate of the heartbeat are stored in a further location of the memory. Such stored data is evaluated to determine whether the heartbeat is occuring with a regular rhythm or, if not, is an anomaly. If such an anomaly is detected or the patient has, through a manually operable switch, provided indication of an anomaly or a heart discomfort, the data processor transfers a series of the sampled heart signals to a still further storage location to be stored therein for subsequent read out and display.

BRIEF DESCRIPTION OF THE DRAWINGS

These and other objects and advantages of the present invention will become more apparent by referring to the following detailed description and accompanying drawings, in which:

FIG. 6 is a high-level diagram of the non-real time program as stored within the ROM and as executed by the CPU of the system shown in FIG. 3A;

FIG. 7 shows the various service routines and the manner in which they are related to coordinate the real time tasks for the system of FIG. 3A;

FIGS. 8, 9, 10, and 11 illustrate the monitoring routine as generally shown in FIG. 6;

FIGS. 12 to 17 show the details of the MONITOR$SERVICE routine as generally shown in FIG. 7;

FIGS. 18A, B, C, and D illustrate, in graphical form, the wave shapes of various anomalies that may occur within the patient's ECG signal and their timing; and FIGS. 19A, B, and C illustrate the segments making up valid R-wave forms as detected by the MONITOR$SERVICE routine as shown in FIGS. 12 to 17.

DESCRIPTION OF THE PREFERRED EMBODIMENT

Figure 3A:
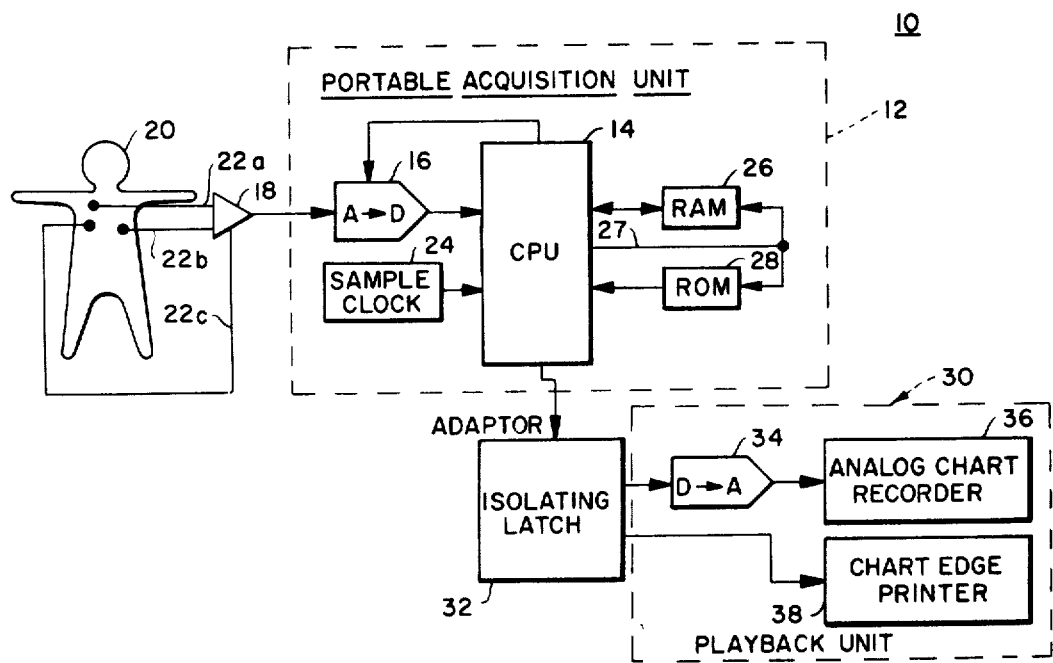
FIGS. 3A and B show, respectively, a high-level functional block diagram of the basic elements of the heart monitoring system in accordance with the teachings of this invention, and a perspective view of the portable data acquisition unit incorporated into the system of FIG. 3A.
Figure 3B:
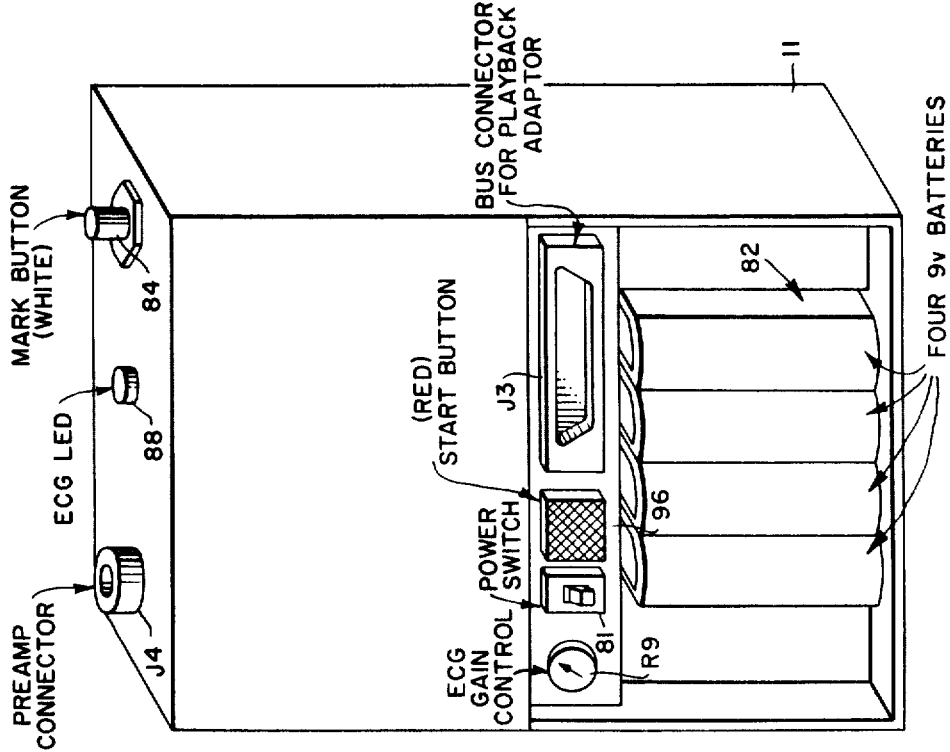

Referring now to the drawings and in particular to FIG. 3A, there is shown a heart monitoring system 10 adapted to be coupled by leads 22a, b, and c to a patient 20 to receive signals to be processed and in particular compacted, before storage in a random access memory (RAM) 26 of a portable acquisition unit 12. The heart monitoring system 10 is capable of monitoring a patient's heart for an extended period of time, e.g., 3 hours and 20 minutes, while continuously processing and in particular compacting data as received in real time for storage in a manner that facilitates the later playback and display by a display unit 30 of the data in a dense from that is readily discernible to the physician. In particular, the patient's ECG signals are continuously monitored to provide heart data in the nature of trends of the average, maximum and minimum heart rates for consecutive intervals, e.g., 5 minutes, throughout the period of data acquisition. In addition, the system further stores data in a form, whereby histograms of the R—R interval difference and heart rate may be displayed. In addition, the heart monitoring system is designed to detect certain arrhythmias of interest and upon dectection, automatically stores a segment of the ECG signal indicative of the detected arrhythmia. After the acquisition period is over, the heart monitoring system 10 is assembled so that the portable acquisition unit 12 is coupled to its playback unit 30 to initiate a readout and display upon its analog chart recorder 36. The playback unit is divided into a first portion known as an adaptor 32 and a second portion including the recorder 36 and a chart edge printer 38. As will be explained in detail later, the edge printer 38 comprises an array of elements for printing a series of marks along the edge of the chart of the recorder 36 to provide an indication of the occurrence of certain events during the monitoring operational for example, the occurrence of a heart anomaly as detected by the acquisition unit 12 would be noted by a mark that would be placed upon an outputted trend chart to designate that interval in which the anomaly occurred. Further, the patient 20, upon sensing heart pain, presses a mark button 84, as shown in FIGS. 3B and 4C, to cause the heart signals occurring during that interval to be identified by a mark provided by the chart edge printer 38. In addition, the printer 38 may provide marks to separate the various charts as are printed out by the recorder 36.

The heart monitoring system is generally shown in FIG, 3A wherein the ECG signals are applied by the loads 22a, b, c from electrodes attached to the patient 20, via a differential preamplifier 18 to the portable acquisition unit 12 and in particular to an A/D converter 16. The signals now in digital form are applied to the central processor unit (CPU) 14. The input of the A/D converter 16 is coupled via the differential amplifier 18 to the connectors 22a and 22b. The differential amplifier 18 includes an ECG preamplifier that buffers the ECG snap connectors 22a and 22b to reduce cable generated artifacts. The ECF preamplifier drives the differential amplifier 18 with a passive ground system. The snap connector 22b is attached to a pre-gelled ECG electrode approximately located at site V5 of the patient's side, whereas the connector 22a is attached to a pre-gelled ECG electrode approximately located at the sternum. These preamplifier connection will produce a positive-going R-wave for most patients. The ground connector 22c is attached to pre-gelled ECG electrode located on the left pectoral region. Though the illustrative embodiment shown in FIG. 3A externally monitors the patient's heart, it is contemplated within the teachings of this invention to connect the sensing electrodes directly to the patient's heart and transmit the detected heart signals from an internally implanted transmitter to an external receiver coupled suitably to the data acquisition unit; the contemplated transmitter and receiver may illustratively take the form of that disclosed in U.S. Pat. No. 4,166,470 assigned to the assignee of this invention.

A clock signal, as derived from a sample clock 24, is applied to the CPU 14 to control the rate at which sample signals are derived from the patient 20. It is understood that the CPU 14 has its own internal clock, as is well known in the art, for controlling its internal operations as well as its interfacing with the other elements of the unit 12. The CPU 14 is coupled by a data-/instruction (I/D) bus 27 to each of a read only memory (ROM) 28 and to the RAM 26. The ROM 28 is adapted to store the instructions which the CPU 14 executes to detect or recognize the input ECG signals, to process these signals including compaction and to appropriately store the processed signal in designated areas of the RAM 26; the programs or routines as stored in the ROM 28 will be explained generally with respect to FIGS. 6 and 7, and in detail with respect to FIGS. 8 to 17. The data as processed and compacted by the CPU 14 is stored in designated areas of the RAM 26 dependent upon the nature of the data, the areas of the RAM 26 in which data is stored are shown in FIG. 5.

The playback unit 30 is optically coupled to an isolating latch or playback adaptor 32 which acts as an isolating digital buffer to receive from the acquisition unit 12 information to be transmitted to and displayed upon the analog chart recorder 36 and the chart edge printer 38. Because of the optical isolation, the patient 20 may be connected to the acquisition unit 12 when the acquisition unit 12 is connected to the line powered playback unit 30 without fear that the patient's ECG signal will be affected by noise or that an electrical shock hazard will be presented to the patient 20. As shown in FIG. 3A, data is applied via a D/A converter 34 to the analog chart recorder 36 which may illustratively take the form of a pen recorder as manufactured by Astromed under their designation Model 102. The latch 32 is also coupled to an edge printer 38 as manufactured by Texas Instruments under their designation EPN 3300.

Figure 5:
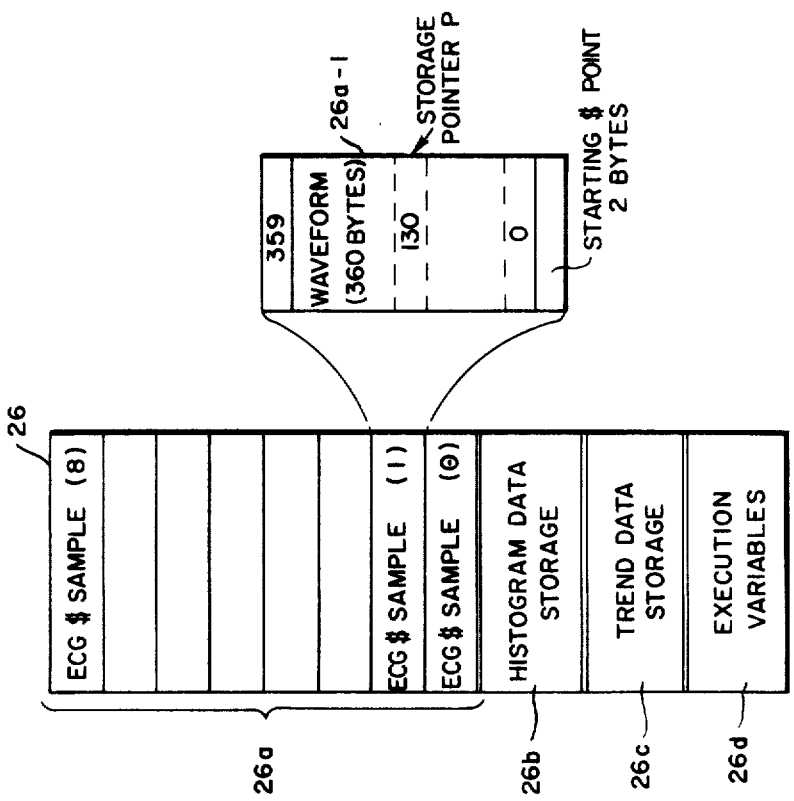
FIG. 5 is a diagram of the storage structure areas of the RAM comprising a memory within the portable data acquisition system as shown in FIG. 3A.

FIG. 5 discloses a data structure or memory map illustrating the manner in which the various types of data are stored in corresponding regions of the RAM 26. As shown in FIG. 5, the RAM 26 includes a first area 26a for receiving ECG data as continuously monitored by the system 10 when disposed in its monitoring mode. In the monitoring mode, as will be explained in detail later, each QRS complex of the patientsECG signal is detected and analyzed to determine whether it is valid, i.e., that it is not noise, and upon occurrence of a valid QRS complex signal, the signal is processed and stored within the first area 26a. It is desired to retain a strip of the ECG signal if there is detected an arrhythmia which may occur after a desired portion of the signal has already been detected. To this end, the first area 26a of the RAM 26 is operated as a pseudo tape loop by storing each sample piece of data in successively lower RAM addresses until the lower limit of a section of the area 26a is reached. At that point, the storage point of address P is returned to the topmost storage location of that section and the next data is overwritten upon the old data. The cycle is repeated continuously until an arrhythmia is detected at which time a pointer to the first/last data boundary is stored and further data storage is inhibited. After the storage is complete,the first/last data pointer or boundary is saved, in a location noted as STARTING$POINT, for directing output of data therefrom. The area 26a of the RAM 26 is divided into a plurality, e.g., nine of buffer sections 26a-0 to 26a-8, each buffer section including a given number (e.g., 360) of consecutive locations wherein data indicating samples of every fourth ECG signal are placed in sequence as indicated above. When one buffer section has been filled, the address or pointer P to the area 26a is moved to designate the topmost location available within the next buffer section. In this manner, nine strips of the ECG signal may be recorded and stored within the RAM 26 to play out and reproduce, as will be explained, a visual display of the ECG signal at that time. Though only nine buffer sections are shown within the area 26a of the RAm 26, it is contemplated that 40 or even more such sections could be incorporated within the area 26a limited only by the size of the desired memory and its cost, and considerations of battery drain. In a further contemplated embodiment of this invention, a single circular buffer section could be used with the data stored therein replicated into permanent storage locations of the RAM 26 upon the detection of a heart anomaly.

The second area 26b is dedicated for storing data to be displayed in a histogram format. In particular, the area 26b is configured illustratively as two arrays of 50 16-bit cells. A first of the 50 -cell arrays is intended for storing an interval difference histogram (IDH), wherein each cell is 4 sample clocks, i.e., 16-⅔ ms. wide. As will be explained later, after the R—R interval has been calculated and the difference between successive intervals obtained, that internal difference is divided by 4, the fractional part being disregarded. The result of the division process is used to point to the appropriate IDH array cell within the first array of the area 26b and that cell is incremented to indicate the occurrence of a difference of that particular order. In an illustrative embodiment of this invention, each of 25 IDH cells is provided on the negative and positive sides of the center to handle differences ranging from 0 to 100 sample clocks, i.e., 0 to 416-⅔ ms. with all differences larger than 416-⅔ ignored. The second 50-cell array of the area 26b is intended for storing the rate histogram, wherein each cell is 5 beats per minute wide. As will be explained later, after the R—R interval has been measured and the equivalent heart rate calculated, that rate is divided by 5, the fractional part being disregarded. The result of the division process is used to point to the appropriate rate histogram cell, and that cell is incremented to indicate the occurrence of that particular interval. The interval difference histogram is primarily used to indicate rhythm instabilities, such as might be produced by atrial flutter, sick-sinus- syndrone, and premature contraction, while the rate histogram indicates the distribution of intervals. By contrast, a trend plot indicates gross changes in interval, as will not be discussed.

Area 26c of the RAM 26 provides a storage area for receiving trend data including three sets of 40 8-bit cells, each cell for storing one of the minimum and maximum of the patient's heart rate and the average of the heart rate as detected during that interval, e.g., 5 minutes. Each set of cells corresponds to a trend interval.

In addition, area 26c provides storage for data indicating whether the mark button 84 was pressed or ECG was stored during a trent sample interval. Typically, if the patient notices some symptom, e.g., dizziness, fainting, or some other discomfort indicative of a heart condition, he may push the mark pushbutton 84 as disposed upon his portable acquisition unit 12 and as shown more specifically in FIGS. 3B and 4C. Upon the actuation of the pushbutton 84, a specific bit pattern is sorted in the cell corresponding to the trend sample interval in which pushbutton 84 was pressed. If an ECG strip was saved in area 26c during a given trend sample interval, the bit pattern in the corresponding cell will be modified to indicate that fact. Upon playback, an indication is made upon the analog chart recorder 36 as to that interval in which the pushbutton 84 was depressed in the form of a mark identifying the time interval, whereby the reviewing physician may identify the time of button depression or ECG sample storage with the corresponding values of minimum, maximum, and average heartbeat rate.

Area 26d provides data storage to receive various variables including state indications and flags that are set during execution of the process.

Figure 4A:
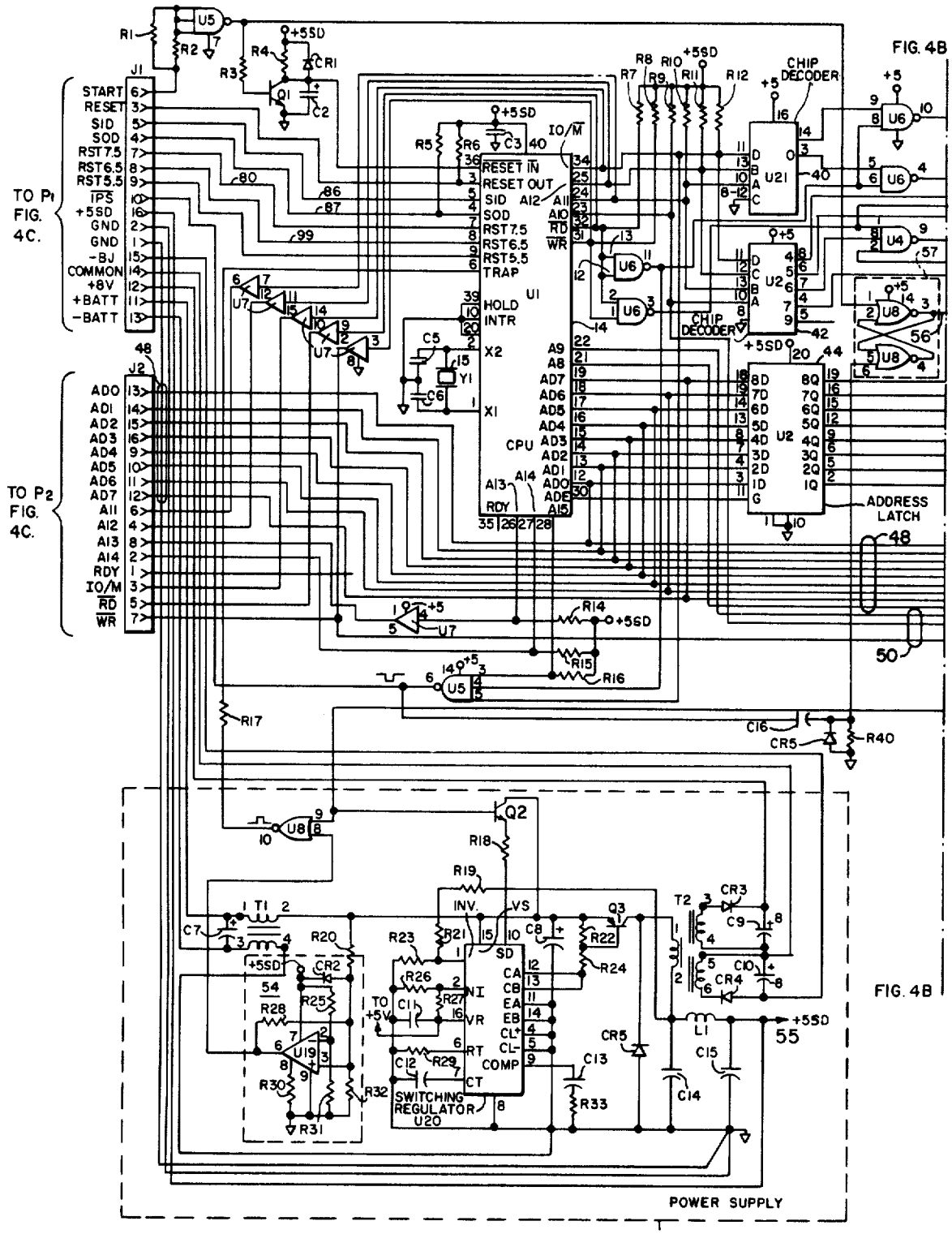
FIGS. 4A, B, C, D and E are detailed circuit diagrams showing the elements of the system generally shown in FIG. 3A.
Figure 4B:
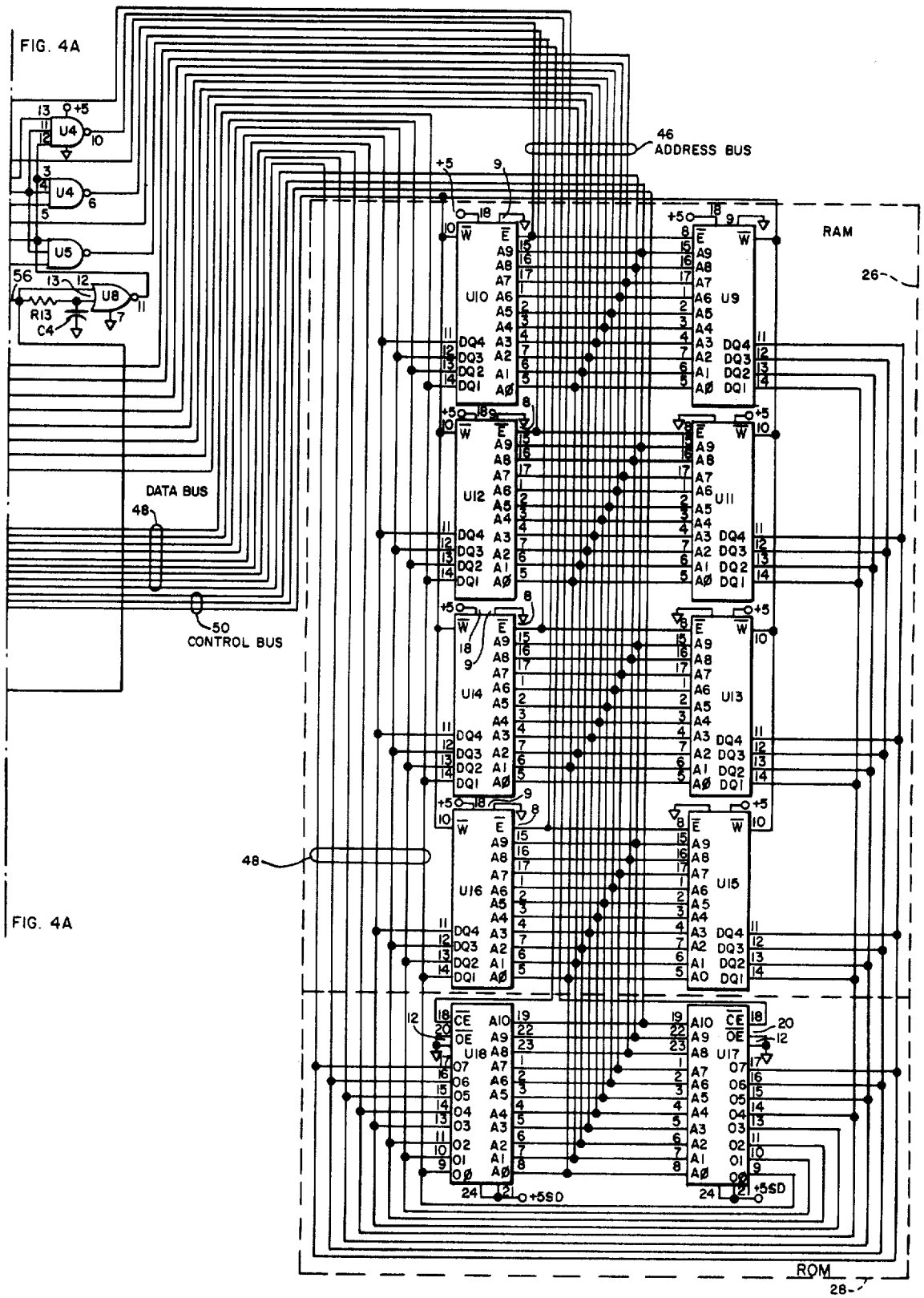
Figure 4C:
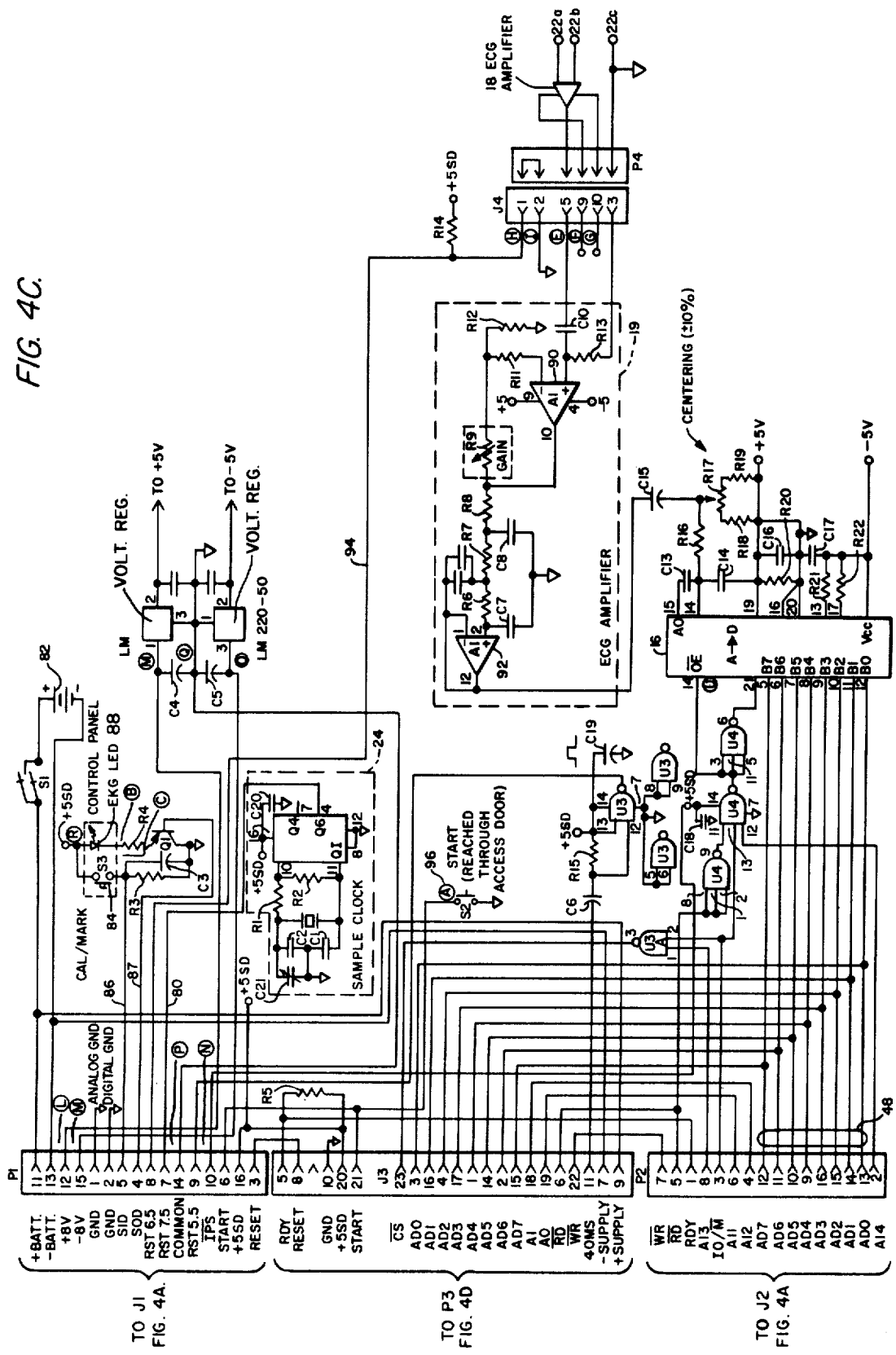

Referring now to FIGS. 4A, B, C, and D, there is shown detailed circuit diagrams of the heart monitoring apparatus 10 as generally shown in FIG. 3A. The data acquisition unit 12 is found principally in FIGS. 4A, 4B, and 4C, wherein there is shown the CPU 14 which may illustratively take the form of a central processing unit manufactured by Intel under their designation 8085A. The CPU 14, in conjunction with address latch 44, receives and transmits data via its address bus 46, control bus 50, the data bus 48, and the connectors J1 and J2. Data is received from the A/D converter 16, as shown in FIG. 4C, and is transferred to and from the RAM 26 via the data bus 48, as shown in FIG. 4A. The RAM 26 is comprised of a plurality of memory elements as manufactured by Harris under their designation No. HM 6514. The data bus 48 is connected to the data transport ports DQ1-4 of each of these elements. The ROM 28 is comprised of two memory elements as manufactured by Intel under their designation 2716 and upon being addressed, instructions of the programs to be described are read out via their output ports 00-07 to be transmitted via the data bus 48 to the CPU 14. As shown in FIGS. 4A and B, addresses are applied via an address bus 46 to the elements of the RAM 26 and of the ROM 28 to address one of the elements and a selected location therein. The CPU 14 generates an initial set of addresses from its outputs A10, 11, and 12 to be applied to a pair of chip or element decoders 40 and 42, illustratively taking the form of a decoder manufactured by RCA under their designation 4028. The outputs of the chip decoders 40 and 42 develop address signals whereby two of the chips or elements of the RAM 26 or one of the elements of ROM 28 is addressed at a time. The particular location within one of the elements of the RAM 26 or the ROM 28 to be addressed is selected by an address latch 44 whose inputs are taken from the ports ADE and AD 0-7 of the CPU 14 to provide output signals applied by the address bus 46 to each of the aforementioned elements to address a selected location therein.

Figure 4D:
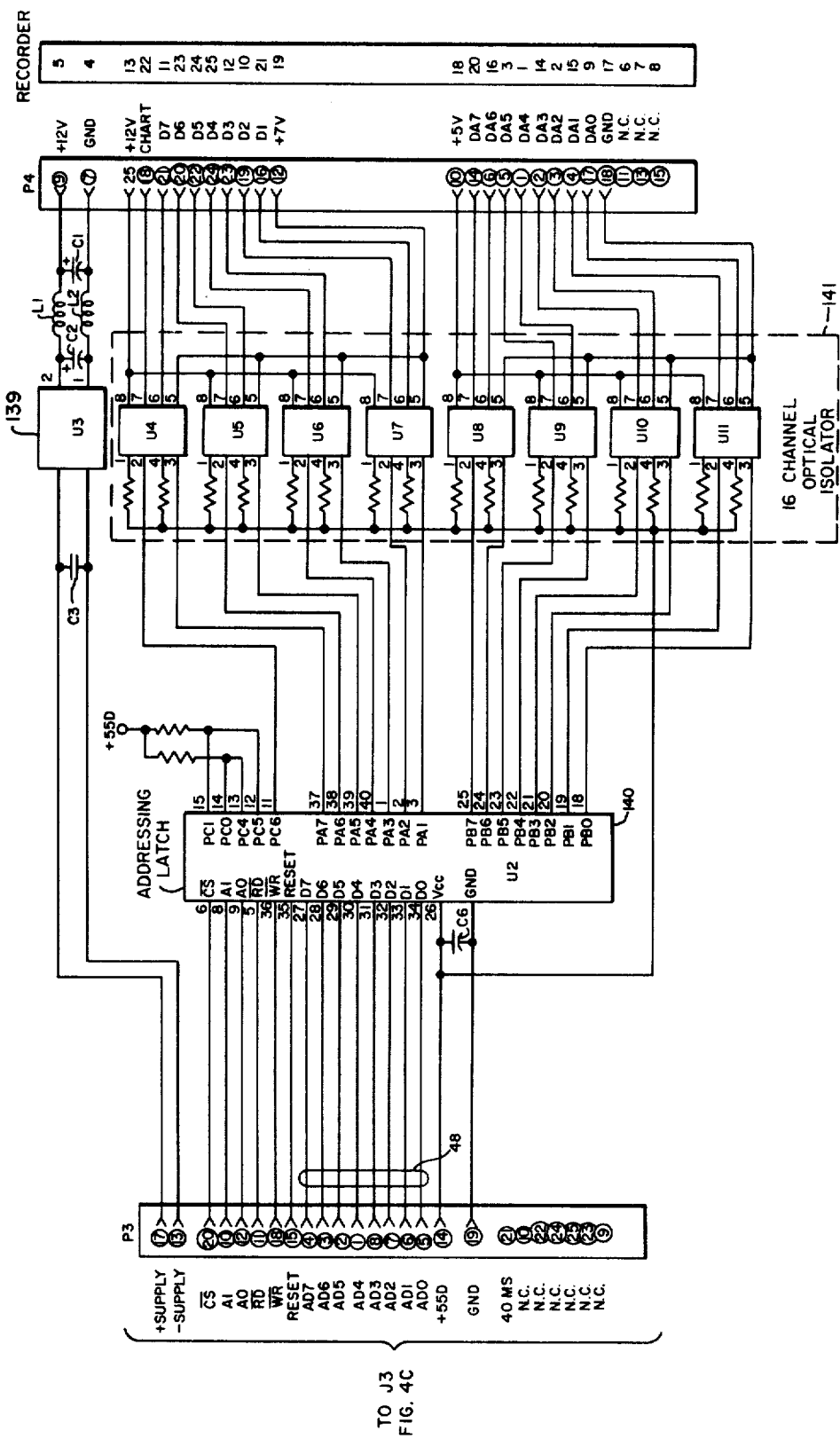

Further command signals are developed from the IO/M to control whether data is to be transferred between the RAM 26 or whether data is to be transferred to the input/output (I/O) and in particular to be transferred via the data bus 48 from the A/D converter 16 (as shown in FIG. 4C) or to transfer data to the addressing latch 149 (as shown in FIG. 4D), which comprises a part of the latch 32 (as shown in FIG. 3A). The ports designated $\overline{RD}$ and $\overline{WR}$ control whether data is to be written onto or read out from the RAM 26. As shown in FIG. 4A, the CPU 14 includes a set of interrupt inputs that are used in a manner, as will be more fully explained, to simplify the programs that are required to implement the various processes and functions of recognition and storage of ECG data. For example, the sample clock 24, as shown in detail in FIG. 4C, applies its sample signal via conductor 80, connectors P1 and J1 to the RST 7.5 interrupt of the CPU 14. The sample clock calls a SAMPLE$ECG$AND$DO$TIMING routine, whereby samples of the ECG signal are taken and the R-wave of the QRS complex is examined to determine whether a valid R-wave is detected to set thereby a R$FLAG, as will be explained with respect to FIGS. 12 to 17.

A further interrupt is made when a voltage detection circuit in the form of a Schmitt trigger 54, a part of the power supply 52, as shown in FIG. 4A, senses that the battery voltage has fallen below a predetermined level. A battery 82, as shown in FIG. 4C, is coupled via connectors P1 and J1 to the power supply 52 and illustratively comprise an 18-volt battery; when the Schmitt trigger 54 senses that the voltage of the battery 82 has fallen below 10 volts, an output is developed and applied to the TRAP interrupt of the CPU 14 to initiate a controlled transfer to a shutdown mode of operation, as will be explained with respect to FIG. 7, wherein only the logic addressing and processing circuitry and the chips of the RAM 26 remain energized, thereby to preserve the energy level of the battery 82. In particular, the Schmitt trigger 54 comprises an operational amplifier U19 that compares the voltage output of the battery 82, normally 18 volts, with the regulated voltage 5SD as provided from the output 55 of the power supply 52, and if the battery voltage falls below a minimum, illustratively 10 volts, the operational amplifier U19 provides a high-going output signal via the NOR gate U8 to the TRAP interrupt of the CPU 14 to thereby initiate the LOW$VOLTAGE$DETECTOR$SERVICE 604, as will be explained with respect to FIG. 7.

The circuitry, as shown in FIG. 4A, of the acquisition unit 12 responds to such a low voltage condition in the following manner. First the A15, IO/$\overline{M}$, and $\overline{RD}$ output terminals of the CPU 14 all go high, causing the NAND gate U5 to apply a low-going output signal to a pulse-shaping circuit comprised of capacitor C16, diode CR5, and resistor R40. The shaped output is in turn applied to set a flip-flop circuit 57 comprised of two NOR gates, each designated by the notation U8. As seen in FIG. 4A, the delayed output 56 of this flip-flop circuit 57 is applied to the power supply 52 via transistor Q1 and also to an array of NAND gates U4 and U5. When transistor Q1 is turned on, a current is applied to a switching regulator U20 that causes power supply 52 to deenergize most elements of the system 10, as will be explained later. In this manner, generally the power supply 52 removes energization from most of the elements of the system 10 while maintaining energization to the various elements of the RAM 26 and further, the array of NAND gates U4 and U5 are disabled to prevent the further application of address signals from the chip decoders 40 and 42 to the RAM 26. In this way, the data previously stored in the elements of the RAM 26 will continue to be stored, and further, addresses and/or spurious signals that may be generated by the CPU 14 and/or the chip decoders 40 and 42 cannot be applied after voltage shutdown to the RAM 26. Further, the output of the flip-flop 57 is applied to drive conductive the transistor Q2 of the power supply 52 whereby a positive-going signal is applied to the SD input of the switching regulator circuit U20, which may illustratively take the form of that regulator manufactured by Silicon General under their designation SG1524. In the normal mode of operation, the regulator U20 periodically energizes the base of the transistor Q3 via its outputs $C_A$ and $C_B$ at a rate to charge capacitor C14 to a desired voltage in the order of +5 volts; the capacitor C14 is repeatedly recharged while tending to be discharged by the load via inductor L1 whereby a substantially constant, regulated +5 volts is applied to its output terminal 55, also designated +5SD. In addition, the periodic voltages are also applied by the primary winding of the transformer T2 to its output secondaries whereby ±8 volts are applied to energize elements of the circuit shown in FIG. 4C. Linear regulator U20 provides at its output $V_R$ a +5 regulated voltage. As can be seen from an examination of FIGS. 4A, B, C, and D, most of the elements of the system 10 are energized by the regulated +5SD voltage as derived from the output 55 of the power supply 52 while it is being operated in its normal, regulating mode. However, when the transistor Q2 is driven conductive upon the occurrence of a low voltage condition, an input signal is applied to the SD input thereby disposing the regulator U20 to the second, non-operative mode whereby the regulated +5SD voltage is removed from most of the elements of the system 10 thereby reducing significantly the drain as applied upon the battery 82. During its shutdown mode of operation, a voltage of +5 volts is only applied by the output terminal VR of the power supply 52 to the various elements of the RAM 26, the chip decoders 40 and 42, the NAND gates U4, U5, and U6, and the flip-flop 57. In particular, the normally applied output from the terminals $C_A$ and $C_B$ of the regulator U20 goes high to render the transistor Q3 non-conductive, thereby disconnecting the voltage from the primary winding of the transformer T2 and the inductor $L_1$, and turning off the output voltage of ±8 derived from the secondary of the transformer T2 and the output derived from the terminal 55. However, as noted above, the regulator U20 continues to apply the +5 voltage from its output $V_R$ to the above-noted elements.

The RST 6.5 interrupt of the CPU 14 is used to detect whether the preamplifier 18 is connected via connector J4 to the portable acquisition unit 12, as shown in FIG. 3. As illustrated in FIG. 4C, the pins 1 and 2 of the connector J4 are connected to the preamplifier connector P4 which has a short across pins 1 and 2 whereby a low or "0" signal is applied via the conductor 94 and connectors P1 and J1 to the RST 6.5 interrupt of the CPU 14. As will be explained with respect to FIG. 7, in the absence of a connection to the ECG preamplifier 18, the system 10 is prevented from entering its monitor or calibration mode of operation.

In the course of either the calibration or monitor modes of operation, a switch 84, as shown in FIG. 4C, may be depressed to apply a signal via conductor 86 and connectors P1 and J1 to the SID input of the CPU 14. In the monitoring mode, the depression of the switch 84 effects a storage of a flag identifying a relatively small interval during the entire monitoring period in which the patient sensed some symptom or felt some discomfort. In the calibration mode, depression of switch 84 causes the refractory period associated with sensing of the QRS to be increased. The SOD terminal of the CPU 14 drives via conductor 87 and connectors J1 and P1 the transistor Q1, as shown in FIG. 4C, whereby the ECG LED 88 is energized. As will be explained, during the calibration modes a potentiometer R9 within the ECG amplifier 19, as shown in FIG. 4C, is adjusted to set the gain of the amplifier 19 to an appropriate level dependent upon the amplitude of the patient's ECG signal. The LED 88 is energized in a manner to indicate when the potentiometer R9 has been appropriately adjusted. A start button 96, as shown in FIG. 4C, is depressed to initiate the operation of the system 10 whereby a low signal is applied to the $\overline{\text{RESET IN}}$ input of the CPU 14. In particular, the start button 96 is depressed to apply a low-going signal via the terminals P1 and J1 to a NAND gate U5, whose output is in turn applied to reset the flip-flop 57. Upon being reset, the flip-flop 57 applies a low signal to deenergize the transistor Q2, whereby the high level applied to the SD input of the switching regulator U20 is removed, permitting regulator U20 to return to the normally energized mode. In addition, the CPU 14 develops an output reset signal that is applied to reset and clear the addressing latch 140, as shown in FIG. 4D.

As shown in FIG. 4A, a computer clock 15 provides a 1.843 MHz clock signal that times the execution of the program by the CPU 14 as well as the various other data transfer functions controlled thereby. As will be explained later, the functions of the CPU 14 including various data transfer functions and calculations are carried out under the control and within the time frame of the computer clock 15, whereas many of the data gathering functions, including the sampling of the patient's ECG signals are carried out in real time under the control of the sample clock 24.

As shown in FIG. 4C, the input ECG signals are applied to the differential ECG preamplifier 18 of a design familiar to those skilled in the art. The output of preamplifier 18 is fed to the ECG amplifier 19 which comprises operational amplifiers 90 and 92 that are connected in series with each other. As mentioned above, the variable potentiometer R9 controls the gain of the ECG amplifier 19. The output of ECG amplifier 19 is applied to the input $I_{in}$ of the A/D converter 16. The converted digital signal is applied from the outputs B0-7 of the A/D converter 16 via the data bus 48 to be selectively stored under the control of the CPU unit 14 within the elements of the RAM 26, as shown in FIGS. 4A and 4B.

Figure 1:
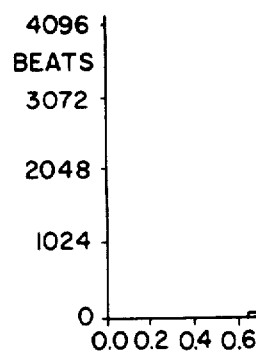
FIGS. 1 and 2 show, respectively, histograms of the R—R interval and of the interval differences, over an extended period of time.
Figure 2:
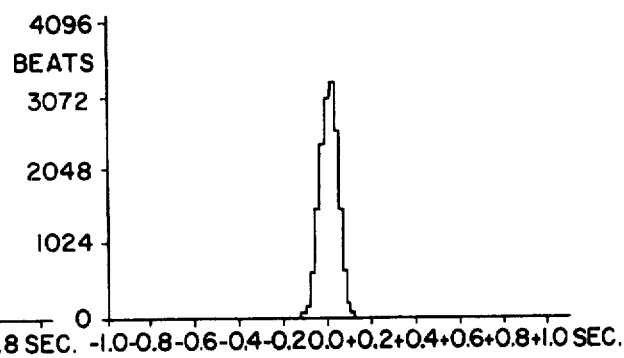
Figure 4E:
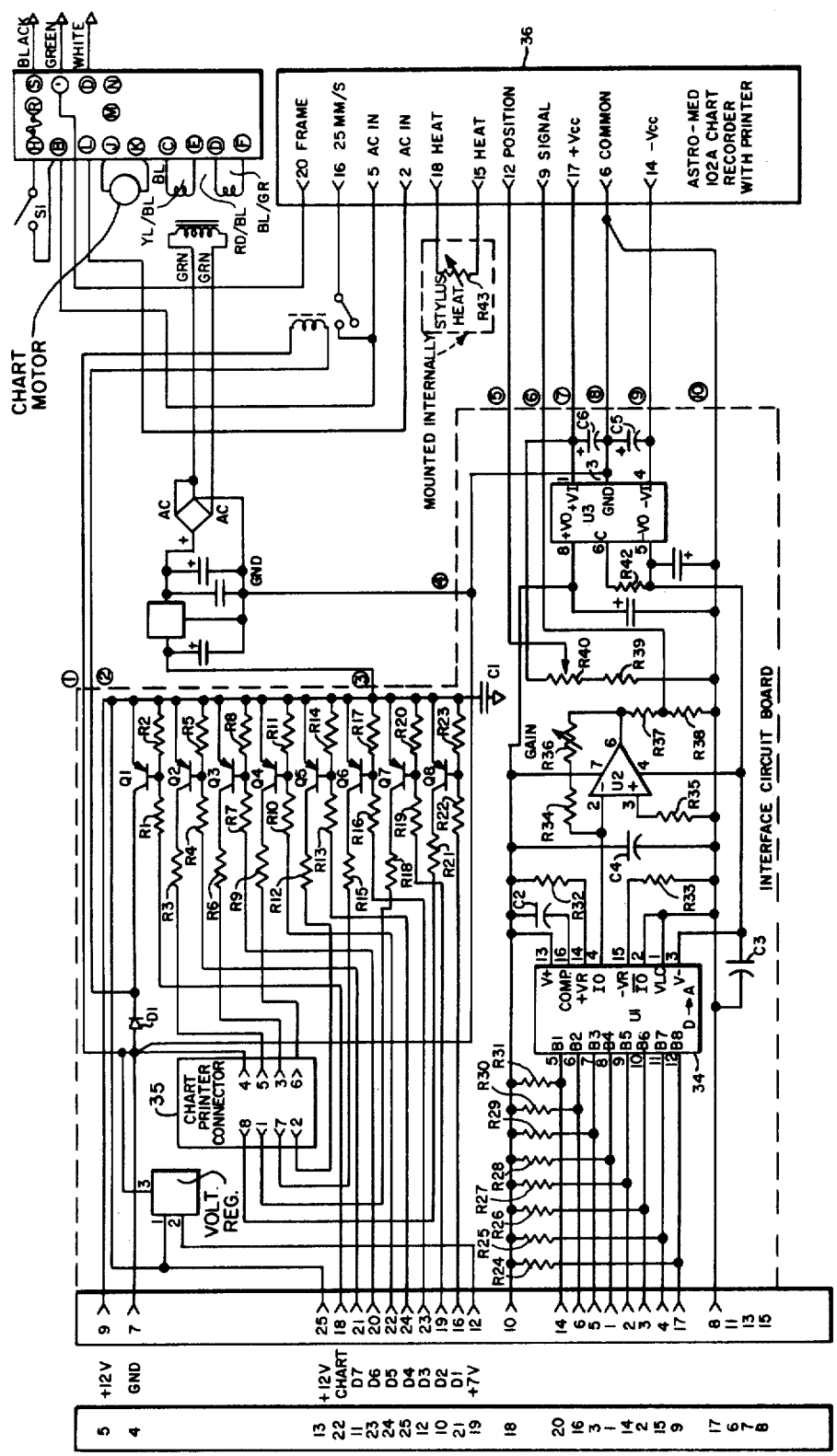

FIGS. 4D and 4E show the isolating latch 32 and the D/A converter 34, generally shown in FIG. 3, as coupled to the analog chart recorder 36 and the chart edge printer 38. The isolating latch 32 is comprised of the addressing latch 140, a 16-channel optical isolator 141, and a DC-DC converter 139. The data to be printed or displayed is applied via the data bus 48 to the inputs D0 to D7 of the addressing latch 140. The latch 140 develops a first set of digital outputs PB0 to PB7 that are applied via the 16-channel optical isolator 141, as shown in FIG. 4D, and the D/A converter 34, as shown in FIG. E, whereby the analog recorder 36 is driven. The latch 140 develops a second set of outputs PA0 to PA7 that are applied to the 7-dot chart printer 38. In particular, the outputs of the latch 140 are applied to an array of dual channel, optical isolators U4 to U11, as shown in FIG. 4D. Isolators U4 to U11 are provided to isolate the analog chart recorder 36 and the chart edge printer 38, which may be powered by a conventional AC outlet, from the data acquisition unit 12 to insure that signals, including the energizing voltage as would be picked up by the recorder 36 and printer 38, will not be applied to either distort the ECG signals as derived from the patient 20 or present a shock hazard to the patient 20. The isolated output signals from the optical isolators corresponding to the outputs PA1 to PA7 and PB0 to PB7 are applied via connector P4 to the D/A converter 34, and to a set of drive transistors Q1 to Q8, respectively. As shown in more detail in FIG. 4E, the collectors of each of the drive transistors Q1 to Q8 are connected to the inputs of the chart printer connector 35. FIG. 4E does not explicitly show the chart edge printer 38, but it is understood that an array of printing elements in the form of heater resistors are incorporated into the analog chart recorder 36 and are energized to selectively print out a mark or marks to highlight the various graphs or presentations of data made thereby. In particular, the analog chart recorder 36 is capable of making a presentation indicative of a R-R interval histogram in a manner similar to that shown in FIG. 1, an interval difference histogram similar to that shown in FIG. 2, and a trend sample showing for a series of consecutive trend sample intervals, e.g., 5 minutes, the minimum/maximum heartbeat rates. In the course of the presentation by the analog chart recorder 36, the chart printer 38 will provide a series of marks on the same paper to indicate the occurrence of various events in a trend sample. For example, a triple mark above a trend sample indicates that the system has detected an anomaly, as will be described in detail later. If the patient 20 senses distress possibly related to his heart activity and in response thereto depresses the mark button 84, the chart edge printer 38 is energized to place a double mark adjacent that trend sample. If excessive noise is imposed upon the ECG signal as derived from the patient 20, the occurrence of that noise will be indicated by the chart edge printer 38 by forming a single mark above the corresponding trend sample. The connector 35 applies via leads to energize the heat resisting elements (not shown) to form the noted marks.

As indicated above, the addressing latch 140 applies a series of outputs PB0 to PB7 via the optical isolators U8 to U11 to the D/A converter 34, which provides an output signal to its $I_o$ output to an operational amplifier U2. In turn, the operational amplifier U2 output is applied to the signal input of the chart recorder 36, whereby its pen is moved to reflect the input analog signal. The circuit as shown in FIG. 4E provides means in the form of the potentiometer R36 whereby an offset may be provided to the signal to be applied to the analog chart recorder 36.

As will be explained later in detail, the particular mode of operation in which the system 10 is disposed is dependent upon which of the elements of the system are connected to the data acquisition unit 12, as shown in FIG. 3A. For example, the system is operative in either a playback mode or a calibration mode if the playback unit 30 is coupled to the portable acquisition unit 12. As shown in FIG. 4D, the addressing latch 140 includes outputs PC1 and PC0 that are set, respectively, high and low by the signals imposed upon the outputs PC5 and PC4. If the connector P3 is in fact coupled to the connector J3, as shown in FIG. 4C, the addressing latch 140 may be accessed to determine the signals imposed upon terminals PC1 and PC0 to thereby set the system 10 to enter either its calibration or playback mode of operation. In addition, inputs are provided from the A11 and A12 outputs of the CPU 14, as shown in FIG. 4A, to the A1 and A0 inputs of the addressing latch 140 to control whether the particular signal as applied via the data bus 48 is to be applied to the chart recorder 36 from its outputs PB0 to PB7 or to the chart edge printer 38 from the outputs PA1 to PA7.

Referring now to FIG. 6, there is shown a high-level flow diagram of the method in which the heart data monitor of this invention operates to record and compact heart data and to playback the stored data in a form that intelligibly informs the physician of the patient's heart condition. Initially, in step 200, the operator depresses the start/reset button 96 upon the control panel of the acquisition unit 12 as shown in FIG. 3B. Thereafter, in step 202, the interrupts to the CPU 14 are disabled. As explained above, the CPU 14 has a variety of interrupt inputs which permit the CPU 14 to take data from different areas of the ROM 28. As will be explained with respect to FIG. 7, the interrupt permits a hardware mechanization of various processes to simplify the software and to effect a saving in time of execution. Initially, these CPU interrupts are disabled. The interrupts are enabled by a series of flags that are disposed within an interrupt array or register within the CPU 14 that permit selected of the CPU's interrupts to be used while disabling the remainder. Initially, each of the CPU's interrupts are disabled until the mode controller for a selected mode enables selected of the CPU's interrupts by applying flags to the corresponding areas of the interrupt array. As a further part of the initialization, signals are applied by the CPU 14 to set the isolating latch 32, permitting data flow to the analog chart recorder 36 and the chart edge printer 38, and to sense whether the playback unit 30 is coupled to the acquisition unit 12. Thereafter, the select step 204 is executed whereby one of the following operating modes is selected: playback (PBKM), calibration (CALIBM), and monitoring (MNTRM). Basically, step 204 looks at the system configuration in terms of which elements are connected to the acquisition unit 12 to determine in which mode the system 10 may be operated. For example, if only the playback unit 30 is coupled to the acquisition unit 12, then step 204 transfers the program to the playback mode by step 300. However, if the playback unit 30 is disconnected from the acquisition unit 12 and the preamplifier 18, and in particular its connector J4, as shown in FIG. 4C, is coupled to the portable acquisition unit 12, the system 10 transfers to the monitoring mode 500 via the initializing step 400. In particular, the connector J4 interconnecting the preamplifier 18 and the acquisition unit 12 has two pins connected together, whereby the RST 6.5 input to the CPU is shorted or rendered to its lowest state, so that an input state is stored in a register of the CPU 14, to be accessed during the select step 204. Similarly, the coupling of the acquisition unit 12 to the playback unit 30 and in particular to the isolating latch 32 is made via the input-output port of the CPU 14 which responds if the isolating latch 32 is coupled to the CPU 14.

Before entering into the monitoring mode 500, it is necessary to check PERMIT$FLAG indicating that the system had been calibrated by the calibration mode 206. Otherwise, if the PERMIT$FLAG is not sensed, the system cannot enter the monitoring mode 500. The MCLEAR routine 400 resets PERMIT$FLAG after directing the process to monitoring mode 500 to prevent reentry into the monitoring mode 500 unless the calibration mode 206 has been rerun to set PERMIT$FLAG. In order to enter the calibration mode 206, it is necessary to detect that the data acquisition unit 12 is connected to both the preamplifier 18 by detecting the shorted pins of its connector J4, as well as to the isolating latch 32. On the other hand, if the data acquisition unit 12 is not coupled to any other device, the system exits immediately to the standby mode 208.

In the calibration mode 206, the CALIBM (calibration mode controller) program is executed to help the operator adjust the system to accept different amplitudes of heart signals and set different refractory periods as are needed to properly detect the QRS complexes of a patient. In connection with the amplitude of the patient's R-wave, these amplitudes may vary as much as 20:1 within a normal patient population. Thus, to prevent saturation of the A/D converter 16 and to permit it to operate within a range of 30 to 50% of its total capability, it is necessary to set the gain of the operational amplifier 90 (see FIG. 4C) of the ECG amplifier 19 until the normal amplitude of the R-wave is of a height to permit a 2:1 increase of the ECG signal amplitude without reaching the upper or lower count limits of the A/D converter 16. In this mode, the output of the preamplifier 18 is continuously monitorerd via A/D converter 16, to determine whether the deviation from baseline peak, whether negative or positive, exceeds 40 A/D converter units or counts. If the peak input is below this limit, the CALIBM program causes the ECG LED 88, as shown in FIG. 4C, to be left unenergized. If the peak amplitudes result in peak deviations from baseline that exceed a second limit corresponding to 60 units of the A/D converter 16, then the LED 88 is continuously lit. If the peak deviation from baseline measured by the A/D converter 16 is between 40 and 60 units, the LED 88 will flash each time a QRS complex is detected. Normally, it is desired to set the gain of amplifier 90 such that the output of the A/D converter 16 around the baseline deviates about ±50 counts throughout the cardiac cycle. To this end, the variable gain of the input amplifier 90 within the A/D converter 16 is adjusted, via R9, so that the LED 88 flashes on each QRS. In addition, the calibration mode 206 adjusts the refractory period, i.e., the expected period between the R and T waves of the patient's heart signal, during which ECG signals applied to the data acquisition unit 12 will be inputted but not processed to detect QRS complexes. To set the refractory period, the mark button 84 is depressed, whereby a buzz or high frequency signal is imparted to the ECG chart to mark the refractory interval for a period as long as the mark button 84 is depressed. Such a signal is developed by the analog chart recorder 36 and increases in duration every 4 seconds while the operator holds mark button 84 down. The operator holds mark button 84 down until the refractory period indicated by the buzz signal extends to the end of the T wave. As will be explained later, the refractory period is computed in accordance with a SET$REFRACTORY$TIME subroutine dependent upon the length of the last occurring R-R interval and a constant that is changed only during adjustment of the refractory period, i.e., the corresponding count of the refractory period counter in turn sets the refractory calibration constant which is used in the calculation of the refractory period upon successive occurrences of the R-R interval.

After calibration, as indicated by the setting of the PERMIT$FLAG, and the detection that the data acquisition unit 12 is coupled to the preamplifier 18, the select step 204 branches to the clear/initializing routine 400, executing the MCLEAR program wherein the storage areas as shown in FIG. 5 except the refractory constant, are cleared in preparation to entering the monitoring mode 500. The monitoring mode 500 will be explained later with respect to FIGS. 8, 9, 10, and 11, and is controlled by the MNTRM program to detect successive QRS complexes, to determine whether such complexes are valid or not, to characterize valid QRS complexes, to measure R-R intervals, and to control the processing of such data and the subsequent storage of the processed data within the RAM 26. The R-R interval is computed and the corresponding rate is obtained before storage within areas 26c of the RAM 26, as shown in FIG. 5. Next, the differences between the successively calculated R-R intervals are calculated to increment one of the bins within area 26b of the RAM 26. Further, there is included a classification subroutine to sense abnormal or arrhythmic heart signals; in particular it is determined whether the rate is above 120 or below 40 beats per minute (BPM) or whether there has been a skipped or early beat. If so, the SAVE$FLAG is set and a trigger signal is generated to store the current set or strip of ECG rhythm signals within one of the nine buffers within area 26a of the RAM 26. Shortly after the SAVE$FLAG is set, the data in the current buffer is frozen and the pointer to the address of the storage buffer moves to the next buffer if available within the area 26a.

The monitoring routine 500 controls monitor mode operations; it does not include routines for performing real time tasks such as timing intervals, R-wave detections, and calculating the R-R interval. The real time routines are separate, as shown generally in FIG. 6, in order to simplify the total software requirement of this system. Briefly, real time tasks, including the R-wave detection routine, are entered once for each cycle of the sample clock 24. The monitoring routine 500 is executed as long as a RUN$FLAG remains true. Any of the following events can set RUN$FLAG false, thus terminating the monitor mode: first, the battery for energizing the system 10 may fall below a predetermined level; second, area 26c for receiving the trend data may be filled, i.e., no more data may be stored therein; and third, the connector J4 of the preamplifier 18 may be disconnected. After RUN$FLAG is set false, MNTRM completes final housekeeping tasks in block 500 and transfers control to step 208 wherein the standby mode controller deenergizes all system components except the RAM 26. In particular, upon the completion of each of the steps in routines 300, 206, or 500, the process transfers to the standby mode 208 wherein the interrupts of the CPU 14 are disabled and the data as stored within the RAM 26 is protected from being read out or written upon. Further, the power supply 52 is shut down to all parts of the system 10 with the exception of the power that is supplied to the RAM 26, thereby insuring the data as stored therein is safely continued to be stored. In this fashion, the drain as placed upon the system's battery 82 is minimized to insure maximum battery life.

Further, the select step 204 may directly transfer the process into the standby mode 208 if the terminal of the preamplifier 18 as well as the playback unit 30 are disconnected from the acquisition unit 12.

Further, as shown generally in FIG. 6, a real time interface program 600 is provided that organizes the various tasks required to be performed in real time, for example, the detection of the R-wave, as a service to the mode controller programs that may be executed in computer time. These real time service routines may detect certain conditions which place the system 10 directly into the standby mode 208. Referring now to FIG. 7, the real time interface program 600 is shown in greater detail. Step 602 detects whether the output of the system battery 82 is low and, if so, actuates the CPU 14 to enter a LOW$VOLTAGE$DETECTOR$SERVICE or routine 604, whereby the process is transferred to the standby mode 208. As shown in FIG. 4A, there is included a Schmitt trigger circuit 54 that is coupled to sense the output of the battery 82. In response to detection of its voltage below a predetermined level, e.g., 10 volts, the circuit 54 applies a high or +5 signal to the TRAP input of the CPU 14 causing the CPU 14 to enter the LOW$VOLTAGE$DETECTOR$SERVICE 604. In this service 604, a determination is first made of whether the process is in the monitoring mode 500 and, if so, sets the RUN$FLAG false. As will be explained in detail later with respect to FIG. 8, the monitoring mode 500 responds to the setting of the RUN$FLAG false to insure that the ECG data is completely recorded, that the calculations of the current R-R interval is completed, and that the average of the then obtained R-R intervals is calculated and stored in an appropriate location within the RAM 26. Thereafter, the RAM 26 is shut down in a manner so as not to lose any stored data and to maintain its energization, as will be explained later. The Schmitt circuit 54 actuates the TRAP interrupts of the CPU 14 in this manner to effect an interrupt of the program to its standby mode 208 in order to reduce the programming that would otherwise be required. Step 606 senses the absence of the ECG preamplifier 18 and in particular that terminal J4 associated with the preamplifier 18 is disconnected, i.e., the shorted pins are removed from the RST 6.5 interrupt of the CPU 14, and the RST 6.5 interrupt goes to +5 volts, whreby the CPU 14 initiates a PRE-AMP$STATUS$SERVICE 608 wherein the process may be transferred to the standby mode 208. In particular, if the system is in the monitoring mode 500, the service 608 will force the system to loop until the preamplifier 18 is reconnected to the mark button 84 is pushed, the RUN$FLAG is set false, causing MNTRM to put the system into its standby mode 208. While the system is looping, no further data is stored within the RAM 26 or processed to detect ORS complexes. Further, when the mark button 84 is pushed, the average of the R-R signals received to that point in time is calculated and the pointers stored in various other locations of RAM 26 is reset. If the process is in its calibrate mode 206 of operation, the system transfers directly to the stand by mode of operation 208 upon the sensing that the preamplifier of the ECG is disconnected.

Though but a single mark button 84 is shown in the described specific embodiment of this invention, it is contemplated that a series of such buttons could be incorporated into this system, whereby the patient could more specifically designate the type of sensation that is being felt as to a particular symptom, body function, or activity. In addition, it is contemplated that an accelerometer type device as would be attached to the patient's body could be substituted for the mark button 84 and upon rapid motion of the patient's body, indicative of a high rate of body activity, that switch would be closed, whereby a specific marking bit pattern would be entered into the appropriate storage location of RAM trend storage area 26c. It is further contemplated that activation of mark button 84 can be used to cause a sample of the patient's ECG to be solved, independently of any rhythm criteria.

As shown in FIGS. 4A and C. the sample clock 24 provides a 240 Hz sample clock signal to the RST 7.5 interrupt input of the CPU 14. The sample clock causes the CPU 14 to effect a CRYSTAL$CLOCK$SERVICE 612 whereby the appropriate mode service routine is set, as shown in FIG. 7. In particular, the service 612 checks the current mode of operation, i.e., determines which of the modes 300, 206, or 500 is in operation and, dependent upon the current mode, selects one of the service routines 614, 616, 618, 620, or 622 to execute. In particular, the service 612 examines XCMODE, a mode status variable assigned to a specified location within the RAM 26, to determine whether its value is 0, 1, 2, 3, or 4, corresponding to the service 614, 616, 618, 620, or 622 are carried out in real time and act as an interface between the input signals which are received in real time and the further operations and calculations that are carried out by the corresponding mode controllers in computer time under the control of the clock 15 coupled to the CPU 14.

A CALIBRATION$SERVICE 614 performs in real time the basic system timing necessary to the calibration mode controller (CALIBM) 206. In particular, the service 614 responds to the sample clock to repetitively call the R-wave detecting subroutine whereby the QRS complex of the ECG signal is detected and its amplitude provided. The obtained ECG peak signals are saved and passed to the calibratiom mode controller (CALIBM) 206 that operates in response to the computer clock 15 to determine whether the QRS complex ampoitudes are acceptable. Further, the CALIBRATION$SERVICE 614 also applies the ECG signal and the "buzz" signal as needed to the analog chart recorder 36 to facilitate refractory adjustment as explained above.

The MONITOR$SERVICE 616 acts as a real time interface for the monitoring mode 500, performing basic timing functions, calling the R-wave detecting routine, and effecting the storage of every fourth ECG byte, i.e., its corresponding amplitude, into one of the nine rotating buffers formed within the area 26a of the RAM 26. If during the course of the monitoring mode 500, a flag is set by MNTRM indicating the detection of an arrhythmic signal, the current buffer of the area 26a is saved and the MONITOR$SERVICE 616 develops a pointer to the next buffer, if available, within the area 26a.

Basically, the DATA$CHART$SERVICE 618 provides timing for the various data charts whereby data is output from the RAM 26 at a rate that corresponds to the incremental advance of the paper chart as driven by the recorder 36. For example, each cell of the trend data indicative of the average minimum amd maximum R-R intervals is applied to the chart recorder 36 at a rate that one cell will be displayed per millimeter advance of the paper chart. In this regard, it is noted that the paper chart is advanced one millimeter per 40 ms. To produce such timing, the service 618 is responsive to the output of the sample clock 24 to produce a drive clock to the recorder 36. It is noted that the sample clock may not be simply divided to obtain the desired 40 ms. drive signal but rather a timing subroutine is provided to respond to 10, 10, 9, 10, 9 clock signals to produce corresponding drive advance signals to the recorder 36. The corresponding 48 clock signals occurring over a timing of 200 ms. are precisely equivalent to the occurrence of five 40 ms. intervals. The facts that each drive advance signal is slightly in error does not affect the overall accuracy of the chart provided by the recorder 36.

The DATA$CHART$SERVICE 618 operates in real time to effect a playback of the trend and histogram data stored in the RAM 26 upon the analog chart recorder 36 and the chart edge printer 38. In addition, the service 618 provides a 60 Hz square wave to the analog chart recorder 34 to provide marks between the graphs displayed upon the recorder 34. For example, there is a marked interval between the trend chart and the histogram chart to indicate clearly to the physician a division therebetween.

The positive and negative SLOPE$PLAYBACK SERVICES 620 and 622 respond, respectively, to positive-going and negative-going slopes to the ECG signal samples stored in regions of RAM 26a to interpolate between ECG points to provide a series of straight lines between two adjacent points to produce a smooth-looking curve on the chart recorder 36. A series of straight line segments each 16.67 ms. long between the stored ECG points are used to reproduce an essentially smooth appearing ECG waveform. Realizing that the data acquisition unit 12 is a portable unit and comprises a RAM 26 that has a limited storage capacity, it is desirable to store less than each sample of the patient's ECG signals in order to increase the length of time for which the monitoring system 10 may be used. However, upon playback wherein the stored data within the RAM 26 is read out, it is necessary to interpolate between the points recorded within the RAM 26 to provide a smooth appearing curve.

The monitoring mode 500, as generally shown and described with respect to FIG. 6, is more fully shown in FIG. 8. The select step 204 transfers control to MNTRM 502, the entry point label for the monitor mode controller 500 via the MCLEAR program 400. Control then passes to step 504 to implement a delay for warm-up and to store selected variables within the area 26d of the RAM 26. For example, it is necessary to set the pointer to designate an initial buffer location in the area 26a, in the trend sample area 26c, and in the histogram area 26b. Further, all storage locations in the minimum rate location of the trend data area 26c are set to a maximum value to simplify the steps of the programming required to determine the subsequent minimum hearbeat rate. Further, a count is stored to be counted down by the subsequent occurrences of the sample clock and upon counting down to zero, that corresponding ECG sample is stored within the designated location of area 26a. A variable maned XCMODE, located in RAM 26d, is set to "1" to indicate to block 612 that the system is in monitor mode. Thus, the MONITOR$SERVICE routine 616 will be called to provide the monitor mode controller with appropriate real time services, such as timing and QRS detection, on each positive-going transition of the sample clock. A count to determine the length of the trend interval in terms of a selected number of sample clock signals, is stored in END$OF$TSI to be used, as will be described later, to determine the end of the first trend sample interval. In addition, a lock out time is stored to provide a delay before a flag can be set by MNTRM to effect the permanent storage of data within a buffer of the area 26a.

After storage of these and other variables, the process moves through loop entry label 506 to the decision step 508, which determines whether the RUN$FLAG has been set true or false. As indicated above, the RUN$FLAG is set false if the battery voltage is determined to be low, the connector J4 of the ECG amplifier 18 is disconnected, the trend storage area 26c, or the histogram storage section 26b is filled, or the pointer to designate the buffer within area 26a indicates that all buffers are already full. If the RUN$FLAG is set false, the program moves through step 520 wherein the data in the current trend sample or interval is calculated to provide an average based upon the previously received R-R intervals. Thereafter the process is transferred to the standby mode controller 208 where commands are given to the power supply to deenergize all elements of the system except the RAM 26 and associated chip select logic to continue the storage of the previously recorded data at reduced battery drain.

Figure 9:
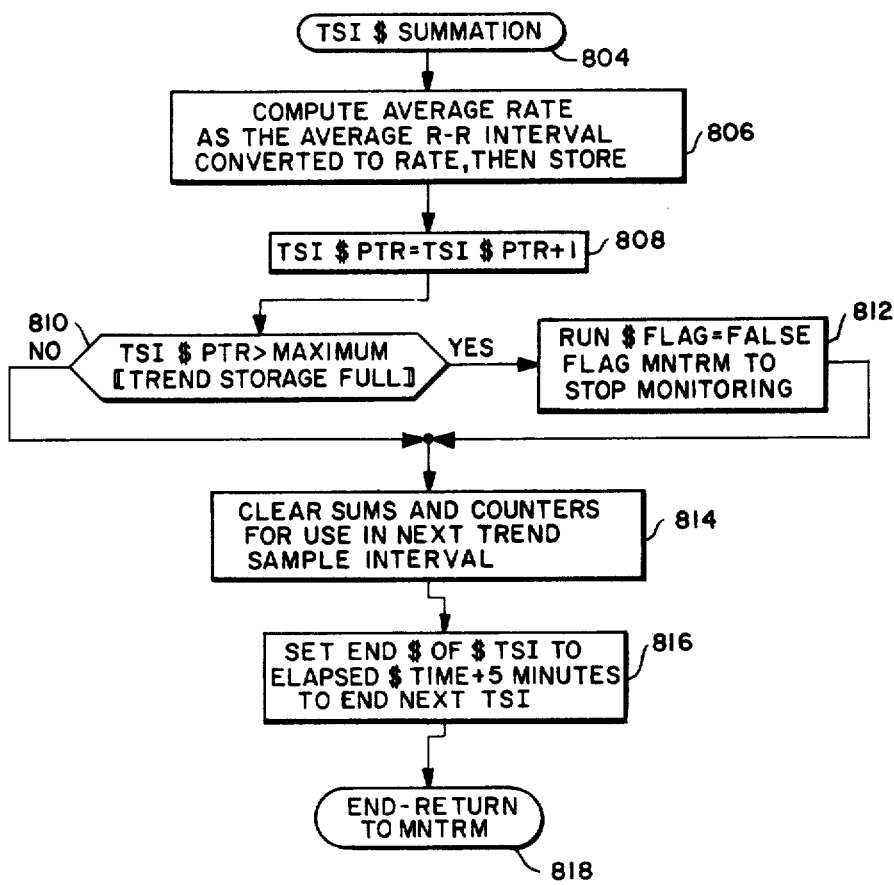

If on the other hand in step 508, the RUN$FLAG is set true, i.e., the system is in a functional condition to receive, process, and store ECG signals, the process moves to step 510 to check whether the mark button 84 has been pressed, and if pressed, step 512 stores an event marker in an auxiliary history array within the RAM 26c indicative of which sample or interval in which the mark button 84 was pressed. Thereafter, after step 512 or if the decision block 510 indicates that the mark button was not pressed, the process moves to step 514 to determine whether the R$FLAG was set true by the execution of the R-wave sensing portion of the MONITOR$SERVICE routine, as will be described with respect to FIG. 16. If yes, the process moves to routine 700 as will be described below in detail with respect to FIG. 10. In routine 700, the data secured by the execution of the MONITOR$SERVICE routine 616, as shown in FIG. 7 and in particular the R-wave sensing routine called thereby, is used to reset the R$FLAG, to process the R$WAVE$TYPE data indicative of the presence of contaminating noise as stored within a designated area of the RAM 26 and to operate on the R-R intervals stored within one of the buffers of RAM 26. After either the routine 700 has been executed or decision step 714 has indicated the R$FLAG to be set false, the process moves to step 518, wherein the ELAPSED$TIME within a trend sample interval is compared with respect to that value END$OF$TSI as stored within area 26d to determine whether the trend sample interval is over, e.g., whether 5 minutes has expired. ELAPSED$TIME is stored within a counter formed within area 26d of the RAM26 and is incremented upon the occurrence of the sample clock. If the interval is over, i.e., yes is indicated by step 518, a routinne 800, as will be explained with respect to FIG. 9, summarizes the data stored in the completed trend sample interval to determine the average R-R interval and therefore the average heartbeat rate and thereafter directs the storage of the R-R interval data to the next location or cell within area 26b. After the decision step 518 has indicated that the trend sample interval has not expired or the completion of the routine 800, the process moves to step 516 wherein the process is halted until the next sample clock occurs and causes execution of the MONITOR$SERVICE routine which inputs and processes the next piece of the ECG data as derived from the patient. Thereafter, the process completes its loop, reentering at label 506 to examine and process the next piece of ECG data.

The summarizing routine 800, as generally shown in FIG. 8, is more fully shown with respect to FIG. 9 wherein the routine 800 is entered via the label 804 to initiate the summarizing process. More specifically, in step 806, the sum of R-R intervals within a single trend sample interval as stored within a storage location of the area 26d is divided by a count indicative of the number of R-R intervals sensed during a single trend sample interval. Thereafter, the average interval is inverted to provide the average rate of the patient's heartbeat during the trend sample interval. Next, in step 808, the pointer TSI$PTR is incremented by "1" to cause the R-R interval data for the next trend sample interval to be stored in the next cell or bin of the area 26c. Thereafter, in step 810, the current pointer TSI$PTR is compared with an indication of the maximum capacity of the area 26c and if in excess of the maximum capacity, the RUN$FLAG is set false in step 812 whereby, as explained above with respect to FIG. 8, step 508 transfers the process via step 520 to the standby mode controller 208. If, as determined by step 810, there is further storage available in area 26c or the RUN$FLAG has been set false by step 812, step 814 clears the counters as formed within area 26d of the RAM 26 and used to count the number of intervals and to sum the intervals occurring during the new current trend sample interval. Thereafter in step 816, the end time indicator of the current trend sample interval, END$OF$TSI, is reset to indicate the next end of trend sample interval by adding 300 seconds to the present value of the ELAPSED$TIME counter. Thereafter, step 818 returns the process of the monitoring routine MNTRM as shown in FIG. 8.

Figure 10:
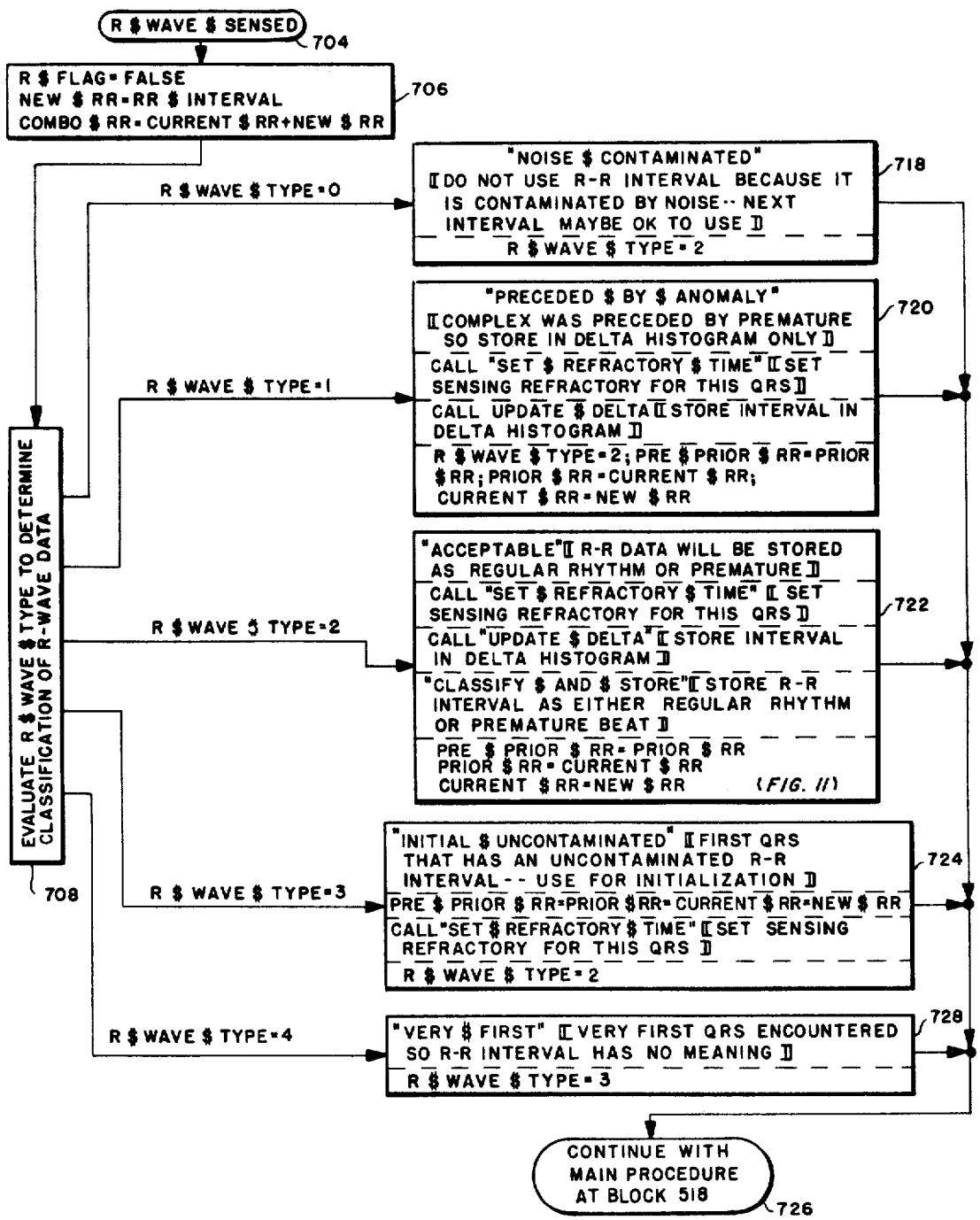

The processing and storing of the R-R data, as generally shown in routine 700 of FIG. 8, is shown in greater detail in FIG. 10. The routine entes via label 704, as shown in FIG. 10, to process and store data pertaining to the R-R interval associated with the QRS complex recently detected by the MONITOR$SERVICE routine 616. In block 706, R$FLAG is set false to acknowledge detection of a QRS complex by MONITOR$SERVICE 616. In addition, block 706 obtains the variable R$WAVE$TYPE, indicative of whether the detected QRS complex is contaminated with noise, and a RR$INTERVAL, indicative of the measured R-R interval. Next, the value of RR$INTERVAL is placed into that location of the area 26d known as NEW$RR. Thereafter, the value of the COMBO$RR is set equal to the sum of CURRENT$RR plus NEW$RR, thereby summing the two most recently recorded values of the R-R intervals.

As will be explained later in detail, the values of NEW$RR corresponding to the most recently calculated R-R interval and of COMBO$RR are used to determine whether to save a strip or set of the patient's ECG signal corresponding to detection of an anomaly, as will be explained with respect to FIG. 11. It is necessary to classify R-wave data so the intervals associated with valid R-wave signals are processed while noise contaminated signals are ignored. In addition, intervals following a premature beat should be treated in a different manner than intervals occurring in a regular rhythm. As shown in FIG. 10, there is provided step 708 that evaluates a variable R$WAVE$TYPE. The stategy for changing the value of R$WAVE$TYPE, in conjunction with block 708, provides the means for classifying each detected QRS complex. For purposes of illustration, assume that the QRS complexes are not contaminated by noise and that the system has just been turned on, i.e., R$WAVE$TYPE is set to "4". Consequently, when the very first QRS is detected, block 708 passes control to step 728, which does not use any R-R intervals information because that information is meaningless when no prior interval has been detected. Since the interval associated with the next QRS complex will have meaning, step 728 sets R$WAVE$TYPE to "3". Consequently, the next uncontaminated complex will be processed by step 724, wherein the detection of the first uncontaminated QRS complex is used to initialize the system to store the subsequent uncontaminated signals. In step 724, the serial locations wherein the most recent values of the R-R interval, namely NEW$RR, CURRENT$RR, PRIOR$RR, and PRE$PRIOR$RR are shifted to place the most recent value of the R-R interval in the NEW$RR RAM location. Thereafter, the SET$REFRACTORY$TIME program is called to set the refractory period as a function of the most recently detected interval between QRS complexes. Thereafter, the R$WAVE$TYPE is set to "2" in order to process the next QRS complex which will be considered to be a normal, uncontaminated QRS signal. After execution of step 724, the program 700 returns via step 726 to step 518 of the monitoring program 500.

Upon the occurrence of detection of the next QRS complex, as indicated by the setting of the R$FLAG signal, the process returns to the subroutine 700 wherein, since R$WAVE$TYPE has been set equal to "2", step 708 directs the program to step 722 wherein an acceptable QRS complex is stored as a regular rhythm or premature signal. The SET$REFRACTORY$TIME subroutine is executed for setting the refractory time as a function of the R-R interval, and thereafter the UPDATE$DELTA subroutine is called to calculate and store the difference between successive R-R intervals in the delta or difference histogram in area 26b of the RAM 26. Thereafter, a CLASSIFY$AND$STORE subroutine, as shown in FIG. 11, is executed to determine whether the detected, uncontaminated QRS is part of a regular rhythm or is a premature beat. If part of a regular rhythm, the R$WAVE$TYPE is left at "2", whereas if the QRS complex occurs early or prematurely, the R$WAVE$TYPE is set equal to "1". The regular rhythm and premature beats will be appropriately processed and stored, as will be explained in conjunction with FIG. 11. Thereafter, the various locations for receiving and storing the R-R intervals are updated with the most recent value of the R-R interval being stored in the NEW$RR location. After completion of step 722, the subroutine 700 exits via step 726 to step 518 of the monitoring program 500.

Upon the detection of the next QRS complex after the setting of the R$WAVE$TYPE equal to "1", step 708, upon sensing the "1" state, transfers control to step 720 wherein the QRS complex that has been preceded by a premature beat is processed. Such a beat is typically known as a compensatory beat and such a beat is not stored within the trend area 26c of the RAM 26. However, the difference between successive R-R intervals is calculated and the UPDATE$DELTA routine is called to store the calculated difference within the IDH array of RAM area 26b. In addition, the refractory period is set by the SET$REFRACTORY$TIME subroutine as a function of the last calculated QRS interval. Thereafter, the R$WAVE$TYPE is set equal to "2" to condition the ACCEPTABLE routine to receive the subsequent, normal QRS complex. In addition, the areas of the RAM 26 for receiving the previously calculated and stored values of the R-R interval are updated with the most recent value of the R-R interval being stored in the NEW$RR location.

In the instance that the MONITOR$SERVICE routine 616 determines that the equal is noise contaminated, MONITOR$SERVICE sets R$WAVE$TYPE to "0", whereby step 708 passes control to step 718 wherein the newly measured R-R interval is not stored because it is contaminated. However, R$WAVE$TYPE is set to "2" to premit initialization of the next uncontaminated QRS complex.

Figure 11:
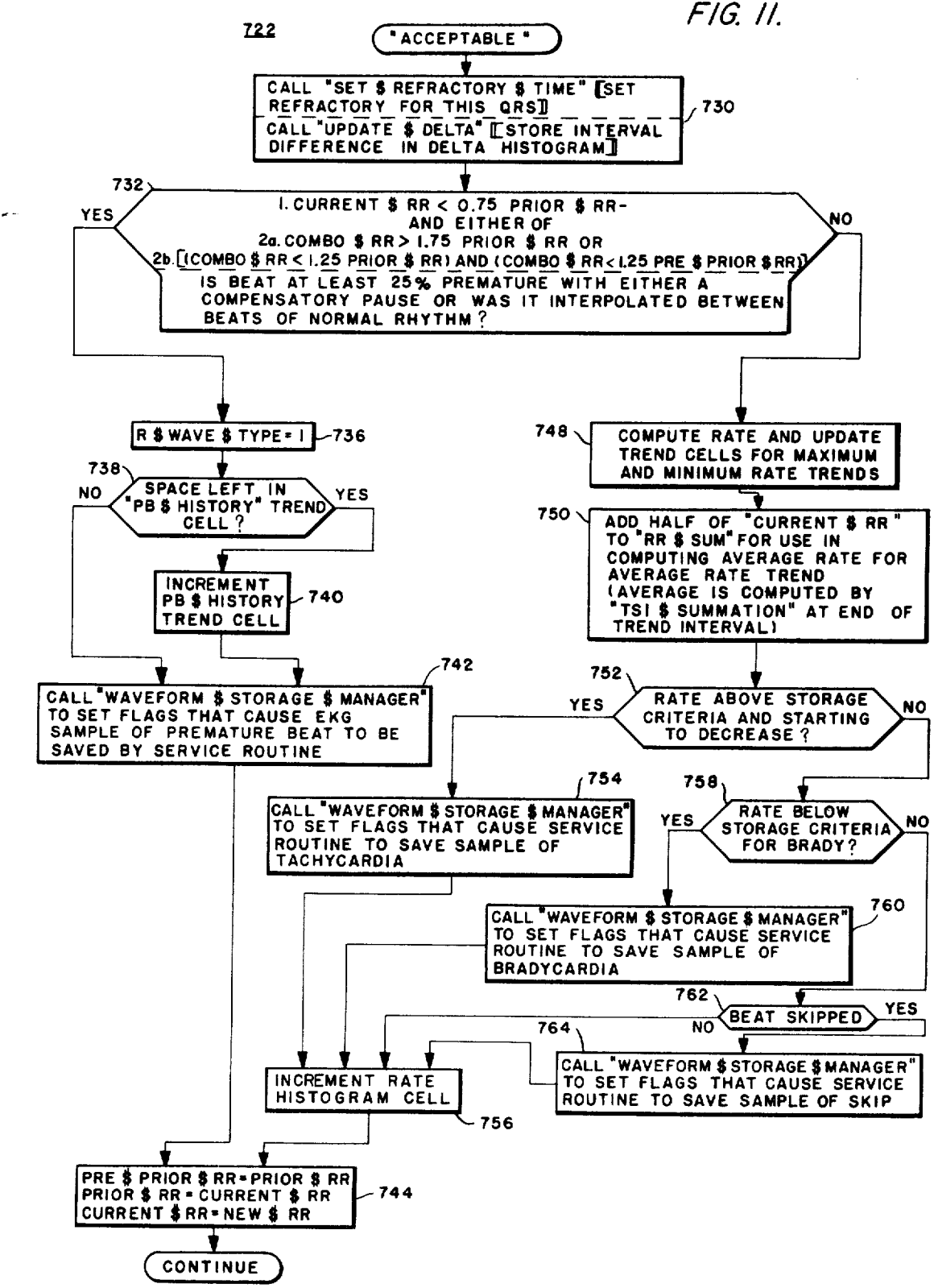

The ACCEPTABLE routine 722, as shown generally in FIG. 10, is described in detail with respect to FIG. 11, for processing the patient's ECG signal and for storing data that has been found to be a valid and acceptable R-wave. The ACCEPTABLE routine 722 begins with step 730, wherein the SET$REFRACTORY$TIME subroutine is called to set the refractory period, wherein the system 10 is disabled from sensing further heart activity or signals placed upon the input leads for that period after the occurrence of the R-wave. Typically, the refractory period for a patient having a heart rate of 75 BPM is in the order of 300 to 400 ms. The refractory period is variably set by the SET $REFRACTORY $TIME subroutine as a function of the previously determined R-R interval as stored within the NEW$RR location within a rotating buffer of area 26d of the RAM 26. As generally described described above, this rotating buffer includes four locations wherein four consecutive values of the most recently determined values of the R-R interval are stored, in order, in the locations NEW$RR, CURRENT$RR, PRIOR$RR, and PRE$PRIOR$RR. As a new value of the R-R interval is calculated or selected, as will be explained with respect to FIG. 16, it is first stored in the NEW$RR location of the noted rotating buffer, and the old values of the R-R intervals are transferred to the next locations. The SET$REFRACTORY$TIME subroutine selects that value of the R-R interval located in the NEW$RR location and, using the following expression, REFRACTORY=KQT (NEW$RR+27)/60, determines the length of the refractory period in terms of sample clock counts as generated by the clock 24. Thereafter in step 730, the subroutine UPDATE$-DELTA is called for determining the difference between adjacent R-R intervals by subtracting the value stored in the PRIOR$RR location from that stored in the CURRENT$RR location. The calculated value of the difference between adjacent R-R intervals is used to define a pointer to a bin or cell within the interval difference histogram array of area 26b of the RAM 26 and that bin is thereafter incremented by "1" to count the occurrence of that difference between the CURRENT$RR and PRIOR$RR intervals.

Decision block 732 is executed to determine whether a premature beat has occurred, based upon the most recent data indicative of the R-R intervals as stored within the NEW$RR, CURRENT$RR, PRIOR$RR, and PRE$PRIOR$RR locations of the noted rotating buffer. In particular, there are two types of premature beats that are detected, a premature beat with compensatory pause and an interpolated beat; these types of beats are detected in that they are attributable to malfunctions of the ventricles and are considered to be more serious than premature beats arising due to malfunctions of the atria. The occurrence of a premature beat with compensatory pause is illustrated in FIG. 18A wherein there is shown a series of R-waves R0, R1, R2, R3, and R4 with the R-wave R0 occurring first in time and the R-wave R4 occurring last in time. As illustrated, the R-wave R3 has occurred early in time, being shifted to the right as seen in FIG. 18A toward R-wave R2; further, the space between R-waves R3 and R4 is greater than normal providing a compensatory pause so that the R-wave R4 occurs at approximately its normally expected time. An interdigitated premature beat is illustrated in FIG. 18C wherein a beat having R-wave R3 is inserted approximately midway between the beats corresponding to waves R4 and R2, noting that the interval between the R-waves R4 and R2 is approximately equal to the normally occurring R-R interval. As will be explained, the subroutine 732 detects whether a premature beat with compensatory pause or interdigitated premature beat has occurred. Premature beat data is processed and stored in a first manner by steps 736 through 742 whereas if no premature beat has occurred, the R-R interval is processed in a second manner by steps 748 through 764.

The determination of whether the beat is premature or not is made by examining the values as stored within the locations NEW$RR, CURRENT$RR, PRIOR$RR, and PRE$PRIOR$RR of the noted rotating buffer in the following manner. Subroutine 732 determines whether a first condition is met, i.e., whether the R-R interval as stored within the CURRENT$RR interval location is less than 75% of that value as stored in the PRIOR$RR location; this comparison can be visualized by examining FIG. 18B, wherein the interval between the R2 and R3 waves is less than 75 percent of the interval between the R1 and R2 waves. Next, to determine the existence of a compensatory pause, the value COMBO$RR, indicative of the sum of the R-R intervals as stored within the NEW$RR and CURRENT$RR locations, is compared with a value indicative of 175% of the R-R interval as stored within the PRIOR$RR location. As shown in FIG. 18B, the length between the R4 and R2 waves is compared to the length between the R1 and R2 waves, and if greater than 1.75 times the length between the R1 and R2 waves, and if the first condition is met, the decision block 732 provides an indication that the beat is a premature beat with compensatory pause by transferring control to step 736.

Second and third tests are made to determine whether an interdigitated premature beat R3, as shown in FIG. 18C, exists. In particular, the value COMBO$RR indicative of the sum of the values within the NEW$RR and the CURRENT$RR locations is determined to be less than 1.25 times the value of the R-R interval as stored within the PRIOR$RR location. As seen in FIG. 18D, this indication compares the total length in time between the R2 wave and the R4 wave to the length between the R1 and R2 waves. Further, a third test is made of whether the values stored in the COMBO$RR location is less than 1.25 of the value of the R-R interval stored within the PRE$PRIOR$RR location. In other words, the length between the R2 ad R4 waves is compared with the length between the R0 and R1 waves to provide an indication of the stability of the heartbeat pattern; if the heartbeat pattern is very irregular, the detected beat may not be a premature beat but an indication of some other, more dangerous anomaly. If the first condition and second and third test results are positive, there is provided an indication by the decision step 732 that an interdigitated premature beat has been detected and the process moves to step 736.

Step 736, shown in FIG. 11, is the start of a premature beat processing routine. Step 736 sets the R$WAVE$-TYPE flag equal to "1", whereby the processed R-wave is noted as an anomaly; as a result, when the STORE$RR$INTERVAL$DATA routine 700 of FIG. 10 is again run, a branch to the PROCESS$ANOMALY subroutine 720 will be executed whereby only the R-R interval data is stored and the system is prepared to receive the next R-wave as an acceptable R-wave. Next, step 738 looks to the location PB$HISTORY within area 26d of the RAM 26 where the number of premature beats for the current trend sample interval is counted and recorded, to determine whether there is space left there for further incrementation. If space is left, the PB$HISTORY location is incremented by one in step 740. In either event, the process moves to step 742, wherein the routine WAVEFORM$STORAGE$-MANAGER is called to initiate processes executed by the MONITOR$SERVICE routine that save a waveform sample containing the premature beat within one of the circulating buffers of area 26a of the RAM 26. In addition to initiating waveform storage, WAVEFORM$STORAGE$MANAGER, step 742, implements a storage lockout system that prevents the waveform storage area 26a of the RAM from being filled up in a few minutes by a "run" of premature beats or other arrhythmias. In particular, when WAVEFORM$-STORAGE$MANAGER is called to store a waveform, it compares the current value of ELAPSED$-TIME with the type of arrhythmias being saved. If the lockout period has not expired, WAVEFORM$-

STORAGE$MANAGER simply returns without initiating a sample save. If the lockout has expired, a sample save will be initiated and the lockout period will be initiated to prevent storage of other similar arrhythmias for 10 minutes by adding 600 seconds to the current time as taken from ELAPSED$TIME to determine that time when the storage of a sample of the particular arrhythmia waveform will be permitted. Thereafter, in step 744, the locations of the rotating buffer are advanced, whereby the R-R intervals as stored in the various indicated locations are set to the next later location and the latest calculated value of the R-R interval is set in the NEW$RR location.

If the decision step 732 decides that the beat or R-wave under investigation is not premature, the process advances to step 748, which is the start of a routine that processes non-premature beats. Step 748 computes the current heartbeat rate by inverting the value of the R-R interval stored within the CURRENT$RR location and, further, the cells within the current bin of the trend sample area 26c are updated for the maximum/minimum rate trends. In particular, the cell locations where the maximum/minimum rate trends are stored, are compared with the current computed value of the heartbeat rate and, if greater or less, respectively, the corresponding bin location is updated with the new maximum or minimum rate. The determination of the maximum and minimum rates of heartbeat provides a statistical indication of the regularity of the heartbeat and, as will be explained, will be displayed for the benefit of the physician. It is also contemplated within the teachings of this invention that the differences between successive intervals of the peak heart activity signal or heartbeat, as are calculated to obtain the interval difference histogram, could also be used in calculations to determine the standard deviations of the interval differences and that such standard deviation could be determined for each trend sample interval and stored in an appropriate location in memory corresponding to that interval. Next in step 750, a portion of the recently selected or calculated value of the R-R interval stored in the CURRENT$RR location is added to that location known as RR$SUM within area 26d of the RAM 26. A portion of the R-R interval, as opposed to using the whole amount, is used to reduce the amount of storage space required for the RR$SUM location. As indicated above, at the end of a particular trend sample interval, the subroutine TSI$SUMMATION is called to calculate the average R-R interval by dividing the sum value of the R-R intervals as stored within the RR$SUM location by the number of samples taken.

Next, as shown in FIG. 11, a determination is made of whether an anomaly other than a premature beat is occurring and in particular whether a tachycardia, a bradycardia, or a skipped beat is present, to set a series of flags whereby that particular sample of the ECG signal corresponding to the anomaly is stored within one of the circulating buffers of the area 26a of the RAM 26. First, in step 752, the most recently calculated value of the heartbeat rate is compared with that maximum rate above which there is an indication that an anomaly known as a tachycardia is occurring within the patient's heart. Further, the step 752 determines whether the rate is increasing by comparing the values of the R-R intervals as stored within the CURRENT$RR and NEW$RR locations and if the values stored in the NEW$RR location is equal to or greater than that stored within the CURRENT$RR location indicating that the rate has begun to decrease, then the process moves to step 754, wherein the subroutine WAVEFORM$STORAGE$MANAGER is called to set those flags whereby a strip of ECG samples indicating the tachycardia is placed within a rotating buffer of area 26a of RAM 26. Illustratively, the selected maximum rate is set at 120 beats per minute. If the most recent value of the heartbeat rate is not above that maximum level, the subroutine moves to step 758, wherein the most recently calculated rate is compared with respect to a minimum rate indicative of the occurrence of a bradycardia and if below the minimum, e.g., 40 BPM, step 760 calls the WAVEFORM$STORAGE$MANAGER subroutine to set those flags whereby a strip of the ECG data illustrating the bradycardia, is stored within a rotating buffer of the RAM area 26a. If not below the noted minimum value, the process moves to step 762, wherein it is determined whether a beat has been skipped. In particular, that value of the R-R interval as stored within the CURRENT$RR location is compared with 1.75 times that value of the R-R interval as stored within the location PRIOR$RR and if greater, there is an indication of a skipped beat whereby the process moves to step 764 to call the WAVEFORM$STORAGE$MANAGER to set flags that cause that strip of the patient's ECG samples to be stored within one of the circulating buffers of area 26a of the RAM 26. After each of the steps 754, 760, 762, and 764, step 756 increments the appropriate rate histogram cell and step 744 updates the values of the R-R intervals within the locations of the rotating buffer, before returning to the MNTRM program and in particular to step 518, as shown in FIG. 8.

Referring now to FIG. 12, the MONITOR$SERVICE routine 616, as generally shown in FIG. 7, will now be described in greater detail. First the SAMPLE$ECG$AND$DO$TIMING routine 800 is called in response to the detection of the sample clock signals as input to the CPU 14; as will be explained in detail later with respect to FIG. 13, a sample of the ECG signal is taken and processed before being stored. Four such samples are stored and then averaged before being placed in a location ECG$BYTE. Further, the routine 800 determines whether an R-wave is present and, if so, sets the R$FLAG true, and further determines if the R-wave is noise contaminated or not; if the R-wave is noise contaminated, the R$WAVE$TYPE is set equal to "0". The SAMPLE$ECG$AND$DO$TIMING routine 800, as generally shown in FIG. 12, is more fully explained with regard to FIGS. 13 to 17. In step 802, it is determined whether the fourth ECG sample has been taken by examining the CLOCK$COUNT and if "0", the corresponding ECG sample is the fourth. In addition, step 802 determines whether there is space available to store the next ECG sample in one of the nine rotating buffers within area 26a of the RAM 26. If it is the fourth sample and there is space available, the process moves to step 804; if not, the process returns via exit point 820 to the main program. In step 804, the average indication of the last four samples is stored within a location of one of the circulating buffers as identified by the pointer LOOP$PTR; thereafter, the LOOP$PTR is incremented to select the next location in the rotating buffer. Thereafter, in step 806, the process looks to see if the SAVE$ECG$FLAG has been set true by WAVEFORM$STORAGE$MANAGER as called from one of the steps 742, 754, 760, or 764 to indicate, respectively, an anomaly such as a tachycardia, bradycardia, or a skipped beat. If SAVE$ECG$-FLAG is set true, the process moves to step 808 wherein the counter LOOP$REMAINING is counted down to permit a given number, e.g., 60, of additional samples of the ECG signal to be stored within the rotating buffer after the anomaly has been detected. In this regard, it is noted that a total of 360 ECG samples are disposed within one of the rotating buffers of the area 26a of the RAM 26. If a no decision is made in step 806, the subroutine 616 returns to the main program.

Step 810 determines whether the rotating buffer has been filled by the ECG data, delaying the execution of the further steps until the 60 samples of the patient's ECG signals occurring after the SAVE$ECG flag is set true have been filled as decided by step 810. If filled, the process moves to step 812 wherein the starting/end pointer within the filled rotating buffer is stored to permit access when it is desired to read out the data stored in that buffer. Further, step 812 sets the storage pointer to the first location of the next available circular buffer within the area 26a of the RAM 26. In step 814, a decision is made as to whether there is a further rotating buffer available within the area 26a, and if no, the RUN$FLAG is set false whereby the MNTRM routine 500 is directed to transfer control to the standby routine 208. If there is a further rotating buffer available, as decided in step 814, step 816 loads the location LOOP$-REMAINING with the predetermined count of the addtional ECG samples, e.g., 60 to be stored after the detection of the anomaly, and thereafter, the SAVE-$ECG flag is set false to terminate the saving of the ECG samples in one of the rotating buffers. Thereafter, the process returns through exit 820 to execute that step of the monitor mode controller program 500 which was interrupted by the sample clock.

As indicated above with respect to FIG. 7, the MONITOR$SERVICE routine is called in response to the occurrence of each of the sample clocks if the system 10, as shown in FIG. 3, is disposed in its mode for monitoring, i.e., the preamplifier 18 is coupled to the data acquisition unit 12. The SAMPLE$ECG$AND-$DO$TIMING routine 800 takes samples of the ECG signal in response to the sample clock occurring at the rate of 240 Hz and determines whether there is present a valid R-wave, as will now be explained in greater detail with respect to FIGS. 13 to 17. Referring now to FIG. 13, the subroutine 800 begins with a timing step 822, wherein the ECG LED 88, as shown in FIG. 4C, is energized for a fixed period, e.g., 40 ms. corresponding to 24 counts of the sample clock, in response to the detection of each R-wave; in particular, 24 counts are loaded into a RAM location LED$TIMER and is decremented until it is set equal to "0", when a command is issued to deenergize the LED 88. In addition, step 822 steps two counters within area 26d of the RAM 26 that serve to time two separate functions. First, the ELAP-SED$TIME location is incremented each second and is used as a system timer that is initiated at the beginning of the monitor or calibration mode; the ELAPSED$-TIME variable is used to control the timing of the trend sample and, in addition, the timing of the lockout period in which further strips of the ECG signals may not be stored, as explained above with respect to the WAVE-FORM$STORAGE$MANAGER routine 742 of FIG. 11. The second clock is formed by the RR$TIMER location and is used to time the R-R interval, i.e., that interval between successive, valid R-waves; the initiation and termination of the RR$TIMER location will be explained below. Next in step 824, an INPUT$AND-$FILTER$ECG routine is called whereby a sample ECG signal is taken and stored in a four location rotating buffer that is incremented each time a new ECG sample is obtained. The ECG data is filtered after a sample is taken by averaging the contents of the four location buffer and storing the result in the location ECG$BYTE. Upon the occurrence of the next sample, the average ECG data stored in the ECG$BYTE location is transferred to the PRIOR$ECG$BYTE location, the rotating buffer is updated, and a new average is stored in ECG$BYTE. ECG$BYTE and PRIOR-$ECG$BYTE will be used, in a manner to be explained, to determine whether a valid R-wave has been detected. Next, in step 826, the process examines the current count of the RR$TIMER to determine whether the refractory period is over and in particular compares the current count of the RR$TIMER to the refractory period determined by the SET$REFRACTORY$-TIME routine, as explained above. If the refractory period is over as determined by step 826, the SEG-MENT$HUNTER routine 900, as will be described more fully with respect to FIG 14, is called to determine the existence of an R-wave segment. After the execution of the SEGMENT$HUNTER routine 900 or there has been indication that the refractory period is not yet over as determined by step 826, step 828 makes a decision as to whether a possible R-wave segment has been found; as will be explained in detail below with respect to FIG. 14, the SEGMENT$HUNTER routine sets the SEGMENT$STATUS location equal to "1" or "2" if a valid segment has been found, or to "3" if a "runt" or short segment has been found; thus, if step 828 finds a "1", "2", or "3" within the SEGMENT$-STATUS location, the process moves to the SEG-MENT$ANALYST routine 1000 wherein the detected segments are compared to determine if a valid R-wave has been detected. After the routine 1000 has been executed or if the SEGMENT$STATUS has been found equal to "0", the process moves to step 830 wherein the SEGMENT$STATUS location is set equal to "0" to prepare the process for the next ECG sample. Thereafter, the process exits via step 832 to complete either the MONITOR$SERVICE routine 616 or the CALIBRA-TION$SERVICE routine 614. In particular, if the system is in monitor mode, the process returns via step 832 to step 802, as shown in FIG. 12.

The SEGMENT$HUNTER routine 900, as generally shown in FIG. 13, is more fully explained with respect to FIG. 14, wherein initially step 902 evaluates the HUNTER$MODE location of RAM 26 to determine the state of the SEGMENT$HUNTER routine 900; initially, the HUNTER$MODE location is set to "0" by the initialization step 504 of the monitoring routine 500. When HUNTER$MODE is set to "0", the process proceeds to step 906 to begin the process of detecting the start of a potential R-wave segment. As shown in FIGS. 19, the QRS complex, of which the R-wave is shown to form a positive-going peak, can be approximated by a series of segments. FIGS. 19A and B show examples of valid R-waves wherein such ECG signals have been represented as a series of three segments. As will be explained below, the existence of a valid R-wave is detected by measuring the time interval between segments, the length, slope, and magnitude of segments, and the number of segments. Initially, in step 906, the time of interval or space between two consecutive segments is measured and, if greater than 62.5 ms., a decision is made that any previously detected segments are part of a deformed QRS complex or noise signal because the maximum interval between two related signal segments has been exceeded. Consequently, the process moves to step 916 wherein the SEGMENT$STATUS location is set equal to "3" to indicate that the maximum interval between two valid segments has been exceeded. If the maximum allowable space between two segments has not timed out as decided by step 906, step 908 stores the current data in a segment start location of the RAM area 26d and initializes the timing of a period corresponding to the maximum length of a valid segment, e.g., 95.8 ms. The current data includes the previous value of the average ECG signal as stored in the PRIOR$ECG$BYTE location, and the current value of time from the RR$TIMER location. Next step 910 determines whether there is a change of slope and if the change of slope is positive by comparing the value stored in ECG$BYTE location and the PRIOR$ECG$BYTE location. If the first value is greater than the second value by a predetermined amount indicating a positive slope greater than a threshold value, then step 912 sets the HUNTER$MODE location equal to "1" to direct the SEGMENT$HUNTER routine 1000, as shown in FIG. 16, to look for the end of that segment. If step 910 makes a "no" decision, step 914 determines whether a segment with a negative slope is present by examining the ECG$BYTE and the PRIOR$ECG$BYTE locations, and if the PRIOR$ECG$BYTE value is greater than that value stored in the ECG$BYTE location by a predetermined amount, there is an indication that a beginning of segment has been found, and the process moves to step 918 wherein the HUNTER$MODE flag is set equal to "2" to direct the SEGMENT$HUNTER routine 1000 to look for an end of that segment. After any of the steps 916, 912, or 918, the process returns to step 828 of the SAMPLE$ECG$AND$DO$TIMING routine 800.

Upon the further calling of the SEGMENT$HUNTER routine 900 and either step 912 or 918 has set the HUNTER$MODE flag equal to "1" or "2", step 902 will sense the particular flag state and direct the process to either of steps 922 or 928 to locate the end of a segment. As an illustrative example, assume that the start of a segment with positive slope was detected on a prior pass through SEGMENT$HUNTER 900 so that HUNTER$MODE flag has been set to "1". Consequently, the evaluation step 902 transfers control to step 922 to locate the end of the segment with the positive slope. First, step 922 checks to see whether there has been a slope reversal or whether the segment duration limit, which was set in step 908, has timed out. If either there has been a slope reversal or the duration of a segment has timed out, the process moves to step 924 wherein the amplitude or magnitude of the segment is calculated in terms of its absolute value and thereafter the SEGMENT$END$HOUSEKEEPING subroutine, as will be further explained with respect to FIG. 15, is executed, whereby the various counters or timers are reinitialized to prepare for recalling the SEGMENT$HUNTER routine 900 to find a new segment. In particular, the step 924 recalls the value of the PRIOR$ECG$BYTE that was initially stored by step 908 at the commencement of detection of the segment and subtracts that value from the PRIOR$ECG$BYTE stored at the detection of the end of the segment to obtain in absolute terms the amplitude from the beginning to the end point of the ECG sample. After step 924 has been completed or step 922 has responded "no" to both inquiries, the SEGMENT$HUNTER routine 900 returns to processing the service procedure step 828.

Upon a subsequent execution of the SEGMENT$HUNTER routine 900 wherein the HUNTER$MODE is set equal to "2", step 902 directs the routine to step 928 wherein the end of a negative slope is determined in a manner similar to that described above. Briefly, step 928 determines whether there has been a slope reversal by examining the PRIOR$ECG$BYTE and ECG$BYTE locations of the rotating buffer and/or whether the segment duration limit has timed out. If either of these conditions is met, the process moves to step 930 wherein the absolute value of the magnitude or amplitude of the segment is determined before calling the SEGMENT$END$HOUSEKEEPING, as will be explained with respect to FIG. 15. Thus, in the SEGMENT$HUNTER routine 900, as explained above with respect to FIG. 14, the beginning and end of a segment as well as its amplitude are detected in preparation for executing the SEGMENT$ANALYST routine 1000 wherein a plurality of such segments will be examined to determine whether the particular combination of segments are so detected makes up a valid R-wave.

Referring now to FIG. 15, there is shown the SEGMENT$END$HOUSEKEEPING subroutine 930 wherein after the calculation of the amplitude of the segment by either step 924 or 930, the various counters and storage locations are initialized in preparation to identify and measure the parameters of the next segment. In particular, step 932 compares the measured values of the duration and magnitude of the detected segment with predetermined minimum values, for example, 15 units or counts of the D/A converter 34, and 16.7 ms. corresponding to four counts of the sample clock 24. If these minimum requirements are exceeded, the process moves to step 934 wherein the value of HUNTER$MODE is transferred to SEGMENT$STATUS to be used, as will be explained, in the execution of the SEGMENT$ANALYST routine 1000. If the minimum requirements are not met as decided by step 932, a further determination is made whether the maximum interval between segments, e.g., 62.5 ms. has elapsed since the end of the last segment; in particular, step 938 compares the current value of the RR$TIMER with the SEGMENT$START$DEADLINE and, if greater, the process moves to step 940 wherein the SEGMENT$STATUS is set to "3" indicating a time out with no valid segment detected. After steps 934 and 940, and if step 938 answers in the negative, the subroutine moves to step 936 wherein the HUNTER$MODE flag is set equal to "0" to prepare for the recalling of the SEGMENT$HUNTER routine 900 to detect the next segment and in particular to detect the beginning of the next segment.

As shown in FIGS. 19A and B, a series of segments can represent valid R-waves. In particular, the QRS complex is defined, in accordance with this invention, by three segments having a particular slope, amplitude, duration, and sequence. As shown generally in FIG. 13, the SEGMENT$HUNTER routine 900 identifies an individual valid segment by obtaining values of its duration, slope, and magnitude, and passes those values to the SEGMENT$ANALYST routine 1000, which stores these values in specific locations, examines the sequence of segments, classifies them as QRS signal or as noise, computes the R-R interval, and resets RR$TIMER. The execution of the SEGMENT- $ANALYST routine 1000 will now be explained in more detail with respect to FIG. 16. Initially, in step 1002, ANALYSIS$MODE is accessed to determine which of the "0", "1", or "2" values that is currently set in that location. In the initializing step 504, as shown in FIG. 8, ANALYSIS$MODE is set equal to "0" so that initially the process will branch to step 1006 wherein the first segment will be obtained and analyzed, as will now be discussed. Upon obtaining the data corresponding to the first segment, step 1006 examines the SEGMENT$STATUS location to determine whether it is less than "3". As was described with respect to step 934 of FIG. 15, SEGMENT$STATUS is set equal to "1" or "2" corresponding to detection of valid segments with positive or negative slopes, respectively; if the space between segments has timed out, the SEGMENT$STATUS flag was set equal to "3" by steps 916 or 940. Thus, if the segment was found by the SEGMENT$HUNTER to be valid, step 1006 stores the segment data in the first segment location within the RAM 26. In particular, the first segment data includes its magnitude, the time the segment began as recorded by the RR$TIMER, the amplitude at its peak as stored in the PRIOR$ECG$BYTE location, and the time at the end of the segment as recorded in the RR$TIMER. In addition, step 1008 changes the ANALYSIS$MODE value from "0" to "1" so that upon the subsequent execution of the step 1002, the SEGMENT$ANALYST routine 1000 moves to step 1012 to evaluate the second segment. First, step 1012 determines whether SEGMENT$STATUS is equal to "3", i.e., a time period in excess of that maximum period corresponding to 62.5 ms. has timed out since the end of the first segment and, if so, step 1014 calls the TREAT$AS$NOISE subroutine 1034 whereby, as will be explained later with regard to FIG. 17, the various storage locations, timers, and counters are reset to erase data corresponding to the first segment to prepare the SEGMENT$ANALYST to receive and analyze the next segment data as a first segment. When step 1012 detects a SEGMENT$STATUS of "3", it indicates that a single segment, as shown in FIG. 19C, has been detected but a second segment has not occurred within the acceptable time limit; therefore, no valid R-wave has been detected.

However, if step 1012 indicates that the status of the second segment is either a "1" or a "2", i.e., not a "3", the process moves to step 1016 wherein a determination is made of whether the first and second segments have the same slope; in particular, step 1016 compares the SEGMENT$STATUS locations of the first and second segments, and if the same, i.e., both segments have the same slope, the process moves to step 1018 wherein the data corresponding to the first and second segments are merged with each other, thus assuming that a large single segment was interrupted by noise or cardiac conduction abnormality and that only a single segment has been detected. In particular, the starting point of the first segment portion is retained, whereas the termination point of the second segment portion is used as the terminating point of the combined first segment. The magnitude of the combined first segment is taken as the sum of the previously determined magnitudes of the first and second segment portions. Further, the ANALYSIS$MODE flag is left as "1" so that upon the reexecution of the SEGMENT$ANALYST routine 1000, the second segment will be obtained and analyzed. On the other hand, if step 1016 determines that the slopes of the first and second segments are different, the identifying data of the second segment in terms of starting and stopping points and magnitude are stored in that location of the RAM 26d for the second segment data; thereafter, the ANALYSIS$MODE flag is set equal to "2" to prepare the SEGMENT$ANALYST routine 1000 to receive and analyze data corresponding to the third segment.

Upon the third reexecution of the SEGMENT&ANALYST routine 1000 with ANALYSIS$MODE set equal to "2," step 1002 transfers the routine 1000 to step 1022, so that the data corresponding to the third segment can be received and analyzed. Step 1022 compares the slope of the current segment with the slope of the previous segment. If the slopes of the successive segments are determined to be the same, step 1024 assumes that the second segment was interrupted and the data corresponding to the current segment is merged into that data of the second segment, i.e., the starting point is taken as that of the second segment, the terminating point is taken as that of the subsequent or current segment, and the amplitude is obtained by summing the amplitudes of the prior and current segment portions. Step 1024 does not change ANALYSIS$MODE from its current value of "2", and thereafter the process returns to continue the service routine at step 830. If the slopes differ, step 1026 stores the current data including starting and stopping points and magnitude in the area 26d of the RAM 26d corresponding to data for the third segment. Thereafter, the ANALYSIS$MODE is set equal to "0" to prepare the SEGMENT$ANALYST routine 1000 to receive and analyze the next sequence of segments.

Thereafter, step 1028 initiates an evaluation of the stored data of the three segments to determine whether a valid or invalid R-wave has been detected. First, step 1028 determines whether the magnitude of the first segment is larger than that of the third segment by comparing the values of magnitude as stored within the assigned locations to the first and third segments. If the first request is greater, the case shown in FIG. 19a, the first two segments, i.e., from point 1 to point 2 and from point 3 to point 4, are recognized as forming the outline of the R-wave, whereby the R-R interval is computed, the RR$TIMER is reset, and the QS duration is computed. In this regard, it is understood that the data for identifying all three segments is obtained at a point in time after the detection and analysis of the segments; therefore, the process of analysis is made be determining when the peak of the R-wave occurred, and in case one, as shown in FIG. 19A, the peak occurs at the end of the first segment and the R-R interval is determined by examining the value of the RR$TIMER at the end of the first segment. In similar fashion, the QS duration is taken as the difference between the beginning of the first segment and the end of the second segment. Further, it is now necessary to reset the RR$TIMER to begin the timing of the next R-R interval. To this end, the RR-TIMER is reset not to zero but to a time corresponding to the interval between the end of the first segment and the end of the third segment. On the other hand, if the first segment is not larger than the third segment corresponding to a second case, as shown in FIG. 19B, the last two segments, i.e., that second segment beginning at point 3 and ending at point 4 and that third segment beginning at point 5 and ending at point 6, are selected as the outline of the R-wave, the R-R interval and QS duration are set accordingly, and the RR$TIMER is reset accordingly. In particular, the peak of the R-wave is selected as the end of the second segment to thereby define the R-R interval as the value of the RR$TIMER at the end of the second segment. Further, the QS duration is thereby defined as the difference between the values of the RR$TIMER taken at the end of the third segment and the beginning of the second segment. The RR$TIMER is set to begin its timing at the beginning of the third segment; more particularly, the RR$TIMER is reset at the end of the third segment to a time corresponding to the length of the third segment to reflect the actual time at the resetting of the RR$TIMER whereby the subsequent R-R interval may be measured. After each of steps 1030 and 1032, a further check is made by step 1033 to determine whether the measured R-wave passes further validity tests; in particular, it is determined that the QS duration is less than 221 ms. and that the determined R-R interval is greater than 242 ms. or 58 counts of the sample clock. It is also contemplated within the teachings of this invention that the average R-R interval, as determined for the corresponding trend sample interval, may be compared with a given limit period to identify the existence of a heart anomaly. If within these limits as determined by step 1033, step 1036 sets the R$FLAG true to indicate detection of the occurrence of a valid R-wave. Thereafter, the ECG LED is turned on for an interval of 83.3 ms. by setting the LED$TIMER for a corresponding period. Then the process continues with the block 830 of the service routine. If the parameters of the detected R-wave do not fall within the noted limits step 1032 calls, in step 1034, the TREAT$AS$NOISE subroutine, as will be explained with respect to FIG. 17.

If the three segments do not occur within a given interval of each other as determined by step 1012 or the QS duration and the R-R interval are not within the predetermined limits as determined by step 1032, the TREAT$AS$NOISE routine 1034 is called, as will be explained with regard to FIG. 17. First, in step 1038, the RR$TIMER is reset to "0" and the ANALYSIS$-MODE is set to "0" to prepare the SEGMENT-$ANALYST routine 1000 to receive and analyze data corresponding to the first segment of a new complex. Thereafter, step 1040 determines whether R$WAVE$-TYPE is greater than "2", and if yes, the routine resets the R$WAVE$TYPE to "4" insuring initialization during the STORE$RR$INTERVAL$DATA subroutine 700, as generally shown in FIG. 8 and in more detail in FIG. 10. If the R-wave is less than or equal to "2", indicative of complete initialization, the R$WAVE$-TYPE is set equal to "0" to insure that the next R-R interval is ignored because it is noise contaminated. After either of steps 1048 or 1042, step 1044 determines whether the system is in its monitor mode by checking the XCMODE and, if yes, the LED 88 is flashed for a period of 41.6 ms. to provide an indication to the operator that noise is being detected; in this regard, this length or duration for flashing the LED 88 is about half the period as would be displayed for energizing the LED 88 in response to detection of a valid R-wave. If the system is not in the monitor mode as determined by step 1044, the system is immediately returned to continue the execution of the SEGMENT$ANALYST routine without flashing the LED 88.

We claim:

1. Apparatus for monitoring and comparing electrical signals indicative of a patient's heart activity, with criteria indicative of regular heart activity comprising a defined relationship between one and a subsequent R-R interval, said apparatus comprising:
   (a) means for measuring in real time a patient's heart activity and for providing a sequence of discrete R-R interval signals, each signal indicative of the time interval between successive peaks of the patient's heart activity;
   (b) means coupled to said monitoring means for receiving the R-R interval signals and for storing a continuously updated set of the R-R interval signals; and
   (c) evaluating means for examining selected of said updated set of R-R intervals with each other in accordance with said defined relationship to provide a manifestation indicative that the patient's heart activity is regular or irregular.

2. Monitoring and comparing apparatus as claimed in claim 1, wherein said evaluating means examines one R—R interval signal with another R—R interval signal displaced in time from said one R—R interval signal, as stored in said storing means.

3. Apparatus for comparing electrical signals indicative of a patient's heart activity, with a set of criteria of regular heart activity comprising a defined relationship between one and a subsequent R—R interval, and for storing the electrical signals indicative of regular heart activity, said apparatus comprising:
   (a) memory means including first, second and third pluralities of storage locations;
   (b) a real time sampling clock and a computer clock;
   (c) means coupled to receive a patient's heart activity and responsive to said sampling clock for sampling at periodic intervals in real time the patient's heart activity signal, and for storing the sampled signals in respective locations of said first plurality, and
   (d) data processing means comprising means responsive to the output of the said computer clock and for providing and storing a series of R—R interval signals in corresponding storage locations of said second plurality, each indicative of the time interval between the successive peaks of the patient's heart activity, and means for examining selected of said series of R—R interval signals as stored in said second plurality of storage locations with each other in accordance with said defined relationship to provide a manifestation indicative that the patient's heart signals are regular or irregular, and means responsive to said manifestation for storing regular heart signals in corresponding storage locations of said third plurality.

4. Comparing and storing apparatus as claimed in claim 3, wherein said storing means stores the processed R—R interval signals in said storage locations of said second plurality in a manner to be readily read out.

5. Comparing and storing apparatus as claimed in claim 4, wherein there is included display means, and said data processing means includes means for reading data from the locations of said second plurality in a manner to be readily displayed upon said display means.

6. Comparing and storing apparatus as claimed in claim 3, wherein the earliest sampled signal is being cleared from its location of said first plurality as the most recently sampled signal is being stored in the current, addressed location of said first plurality, and said data processing means comprises means responsive to an irregular manifestation for permanently storing a series of the sampled heart activity signals in the locations of said first plurality.

7. Apparatus for evaluating electrical signals indicative of a patient's heart activity, with a set of criteria of regular heart activity comprising a defined relationship between one and a subsequent R—R interval, said apparatus comprising:
(a) a real time sampling clock;
(b) a computer time clock;
(c) means coupled to receive a patient's heart activity signal and responsive to the output of said sampling clock for sampling at periodic intervals the patient's heart activity signal, and
(d) data processing means comprising means responsive to said output of said sampling clock and to said sampled heart activity signals to provide a series of R—R interval signals, each indicative of the time interval between successive peaks of the patient's heart activity, and means responsive to the output of said computer clock for examining selected of said series of R—R interval signals with each other in accordance with said defined relationship to provide a manifestation indicative that the patient's heart signals are regular.

8. Apparatus for monitoring over a prolonged monitoring period and evaluating electrical signals indicative of a patient's heart activity with a set of criteria indicative of the waveform of a QRS complex, said apparatus comprising:
(a) a real time sampling clock;
(b) a computer time clock;
(c) sampling means responsive to the output of said sampling clock for sampling the patient's heart activity signal to provide a sequence of sampled heart signals of a single QRS complex; and
(d) data processing means comprising means responsive to said output of said sampling clock for comparing one sampled heart signal with a subsequent sampled heart signal of the same QRS complex to determine whether the relationship therebetween meets said criteria of a valid QRS complex waveform, and means responsive to the output of said computer time clock for further processing valid sampled heart signals.

9. Monitoring and evaluating apparatus as claimed in claim 8, wherein there is included memory means comprising a first plurality of storage locations for receiving and storing respectively said sequence of sampled heart signals, and a second plurality of storage locations, said comparing means comprises means for identifying a sequence of the valid, sampled heart signals as a segment of a plurality of segments comprising a single QRS complex, and for storing data indicative of an identified segment in a corresponding location of said second plurality.

10. Monitoring and evaluating apparatus as claimed in claim 9, wherein said data processing means comprises means for evaluating the segment identifying data stored in the locations of said second plurality to determine whether a detected and processed combination of the segments forms a valid QRS complex of the patient, and if so, for providing a second manifestation thereof.

11. Monitoring and evaluating apparatus as claimed in claim 10, wherein said data processing means includes means for accessing the segment identifying data as stored in the locations of said second plurality and for determining the intervals between the valid heartbeats.

12. Monitoring and evaluating apparatus as claimed in claim 11, wherein said memory means comprises a third plurality of storage locations, each location of said third plurality for receiving and storing data indicative of the interval between successive heartbeats, and said data processing means comprises means responsive to the output of said computer clock for examining adjacent locations of said third plurality to determine whether a valid QRS complex occurs at a regular rhythm and, if not, to provide a third manifestation of a heart anomaly.

13. Monitoring and evaluating apparatus as claimed in claim 12, wherein said examining means determines whether the valid heartbeat signal occurs prematurely to provide the third manifestation indicative of a premature heartbeat.

14. Monitoring and evaluating apparatus as claimed in claim 12, wherein said examining means determines whether the valid heartbeat signal occurs outside of an expected interval to provide the third manifestation indicative of a delayed or skipped heartbeat.

15. Monitoring and evaluating apparatus as claimed in claim 12, wherein said examining means compares the determined interval with respect to a maximum value thereof and, if exceeded, to provide a fourth manifestation of a heart anomaly.

16. Monitoring and evaluating apparatus as claimed in claim 15, wherein said examining means compares the interval with a predetermined minimum value thereof and if less, provides a fifth manifestation of a heart anomaly.

17. Monitoring and evaluating apparatus as claimed in claim 17, wherein there is further included sensor means responsive to a body function of the patient for providing a sixth manifestation thereof.

18. Monitoring and evaluating apparatus as claimed in claim 17, wherein said data processing apparatus comprises means responsive to each of said third, fourth, fifth, or sixth manifestations for effecting the permanent storage of the heart activity sample signals in the storage locations of said first plurality.

19. Monitoring and evaluating apparatus as claimed in claim 12, wherein said memory means comprises a fourth plurality of storage locations, each location of said fourth plurality for receiving data indicative of the patient's heart activity and said data processing means comprises means responsive to the output of said computer clock for storing the heart activity data in a compressed format that facilitates readout and display.

20. Monitoring and evaluating apparatus as claimed in claim 19, wherein said monitoring period comprises a plurality of consecutive trend sample intervals, each location of said fourth plurality stores heart activity data corresponding to one of a plurality of consecutive trend sample intervals, and said data processing means comprises address means for selecting and storing the heart activity data into the current location of said fourth plurality.

21. Monitoring and evaluating apparatus as claimed in claim 19, wherein each location of said fourth plurality corresponds to a range of a particular characteristic of the heart activity data, and said data processing means comprises means for addressing a particular location of said fourth plurality in accordance with the particular detected range of the heart activity data.

22. Monitoring and evaluating apparatus as claimed in claim 21, wherein said characteristic includes an indication of the patient's heartbeat rate.

23. Monitoring and evaluating apparatus as claimed in claim 21, wherein said characteristic includes the difference between the intervals associated with successive heartbeats.

24. Monitoring and evaluating apparatus as claimed in claim 19, wherein the addressed, current location of said third plurality receives the currently determined interval between successive heartbeats as it is being calculated while the earliest determined interval signal is being cleared.

25. Apparatus for monitoring and comparing electrical signals indicative of a patient's heart activity, with a set of criteria of regular heart activity comprising a defined relationship between one and a subsequent R-R interval, said apparatus comprising:
   (a) means responsive to a patient's heart activity for providing a series of R-R interval signals, each indicative of the time interval between the successive peaks of the patient's heart activity; and
   (b) evaluating means for examining selected of said series of R-R interval signals with each other in accordance with said defined relationship to provide a first manifestation indicative that the patient's heart signals are regular or irregular, said evaluating means comprises means for comparing the current R-R interval signal with respect to a maximum value thereof and if exceeded, to provide a second manifestation that the patient's heart signals are irregular.

26. Monitoring and comparing apparatus as claimed in claim 25, wherein said evaluating means comprises means for comparing the current R-R interval signal with a predetermined minimum value thereof and if less, for providing a third manifestation indicative that the patient's heart signals are irregular.

27. Monitoring and comparing apparatus as claimed in claim 26, wherein there is included means for providing an average value of said series of R-R interval signals, and said evaluating means comprises means for comparing said average value with a predetermined value and if less, for providing a fourth manifestation indicative that the patient's heart signals are irregular.

28. Monitoring and comparing apparatus as claimed in claim 27, wherein said evaluating means comprises means for comparing said average value with a predetermined maximum value and if greater, for providing a fifth manifestation indicative that the patient's heart signals are irregular.

29. Monitoring and comparing apparatus as claimed in claim 28, wherein there is included a first plurality of storage locations and a second plurality of storage locations, means for sampling the patient's heart activity and for storing the samples thereof in corresponding locations of said first plurality, and means responsive to one of said third, fourth or fifth manifestations for effecting the permanent storage of the heart activity sample signals in said storage locations of said first plurality.

30. Monitoring and comparing apparatus as claimed in claim 29, wherein there is included means responsive to a manifestation indicative that the patient's heart signals are regular for storing the heart activity signals in corresponding storage locations of said first plurality in a compressed format that facilitates readout and display.

31. Monitoring and comparing apparatus as claimed in claim 29, and as adapted to monitor the patient's heart activity for a prolonged period comprising a plurality of consecutive trend sample intervals wherein each location of said second plurality stores heart activity signals corresponding to one of a plurality of consecutive trend sample intervals, and there is further included address means for disposing the heart activity signals into a current storage location of said second plurality.

32. Monitoring and comparing apparatus as claimed in claim 29, wherein each location of said second plurality corresponds to a range of a particular characteristic of the heart activity signals and there is further included address means for addressing a particular location of said second plurality in accordance with the particular detected range of the heart activity signal.

33. Monitoring and comparing apparatus as claimed in claim 32, wherein said characteristic is said time interval between successive peaks of the patient's heart activity.

34. Monitoring and comparing apparatus as claimed in claim 33, wherein said characteristic includes the difference between successive R-R interval signals.

35. Monitoring and comparing apparatus as claimed in claim 34, wherein said addressed, current storage location of said second plurality receives the currently determined R-R interval signal, while the earliest determined R-R interval signal is being cleared.

36. Apparatus for monitoring and comparing electrical signals indicative of a patient's heart activity, with a set of criteria of regular heart activity comprising a defined relationship between one and a subsequent R-R interval, said apparatus comprising:
   (a) means responsive to a patient's heart activity for providing a series of R-R interval signals, each indicative of the time interval between the successive peaks of the patient's heart activity; and
   (b) evaluating means for examining selected of said series of R-R interval signals with each other in accordance with said defined relationship to provide a manifestation indicative that the patient's heart signals are regular or irregular, said evaluating means comprises means for determining whether the value of a first occurring interval is less than that of a subsequent interval by a predetermined amount and, if so, to provide the manifestation indicating the existence of a premature heartbeart.

37. Monitoring and comparing apparatus as claimed in claim 36, wherein there is included means for adding the values of first and second occurring intervals to provide a summed interval manifestation, and said evaluating means comprises means for comparing said summed interval manifestation with a value of a third interval occurring after the second interval and if greater than a predetermined portion thereof, for providing a second manifestation indicating the existence of a premature beat with compensatory pause.

38. Monitoring and comparing apparatus as claimed in claim 37, wherein said comparing means compares said summed interval manifestation with the value of a third later occurring interval, and if less than a predetermined factor times the value of the third interval and said summed interval manifestation is less than a predetermined factor times the value of a fourth occurring interval for providing a third manifestation of an interdigitated premature beat.

39. Apparatus for monitoring and comparing electrical signals indicative of a patient's heart activity, with a set of criteria of regular heart activity comprising a defined relationship between one and a subsequent R-R interval, said apparatus comprising:
   (a) means responsive to a patient's heart activity for providing a series of R-R interval signals, each indicative of the time interval between the successive peaks of the patient's heart activity; and (b) evaluating means for examining selected of said series of R-R interval signals with each other in accordance with said defined relationship to provide a manifestation indicative that the patient's heart signals are regular or irregular, said evaluating means comprises means for comparing the values of successive R-R interval signals to provide the manifestation indicative of a premature beat.

* * * * *